US012013453B2

(12) United States Patent
Boskamp et al.

(10) Patent No.: US 12,013,453 B2
(45) Date of Patent: Jun. 18, 2024

(54) SYSTEMS AND METHODS FOR DETECTING PATIENT MOTION DURING MAGNETIC RESONANCE IMAGING

(71) Applicant: Hyperfine Operations, Inc., Guilford, CT (US)

(72) Inventors: Eddy B. Boskamp, Shelton, CT (US); Mark Joseph Tuccillo, Southington, CT (US); Prantik Kundu, Branford, CT (US); Michael Twieg, New Haven, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 200 days.

(21) Appl. No.: 17/077,850

(22) Filed: Oct. 22, 2020

(65) Prior Publication Data

US 2021/0121094 A1    Apr. 29, 2021

Related U.S. Application Data

(60) Provisional application No. 62/925,865, filed on Oct. 25, 2019.

(51) Int. Cl.
*G01R 33/565* (2006.01)
*A61B 5/00* (2006.01)
*A61B 5/055* (2006.01)
*G01R 33/34* (2006.01)
*G01R 33/58* (2006.01)

(52) U.S. Cl.
CPC ........ *G01R 33/56509* (2013.01); *A61B 5/055* (2013.01); *A61B 5/6803* (2013.01); *G01R 33/34038* (2013.01); *G01R 33/583* (2013.01)

(58) Field of Classification Search
CPC ........ G01R 33/56509; G01R 33/34038; G01R 33/583; A61B 5/055; A61B 5/6803
See application file for complete search history.

(56) References Cited

U.S. PATENT DOCUMENTS

| | | | |
|---|---|---|---|
| 5,284,144 A * | 2/1994 | Delannoy | G01R 33/3628 977/911 |
| 5,498,962 A | 3/1996 | Sepponen | |
| 5,544,653 A | 8/1996 | Takahashi et al. | |

(Continued)

FOREIGN PATENT DOCUMENTS

| | | |
|---|---|---|
| EP | 3486672 A1 | 5/2019 |
| WO | WO 01/12057 A1 | 2/2001 |

OTHER PUBLICATIONS

U.S. Appl. No. 17/077,882, filed Oct. 22, 2020, Boskamp et al.

(Continued)

*Primary Examiner* — Dixomara Vargas
(74) *Attorney, Agent, or Firm* — Foley & Lardner LLP

(57) ABSTRACT

A device and method for detecting motion and position of a patient positioned within a magnetic resonance imaging system, the device including at least one sensor configured to be capacitively coupled to the patient during magnetic resonance imaging. The method includes, while a patient is positioned within a magnetic resonance imaging system, measuring a reflected power value indicative of an amount of power reflected by the at least one sensor in response to being driven by at least one RF signal, and determining, using the reflected power value, whether the patient has moved.

29 Claims, 18 Drawing Sheets

(56) References Cited

U.S. PATENT DOCUMENTS

| | | | |
|---|---|---|---|
| 7,122,012 B2 | 10/2006 | Bouton et al. | |
| 7,999,548 B1* | 8/2011 | Brown | G01R 33/3678 |
| | | | 324/309 |
| 9,541,616 B2 | 1/2017 | Rothberg et al. | |
| 9,547,057 B2 | 1/2017 | Rearick et al. | |
| 9,606,209 B2 | 3/2017 | Ernst et al. | |
| 9,625,544 B2 | 4/2017 | Poole et al. | |
| 9,645,210 B2 | 5/2017 | McNulty et al. | |
| 9,817,093 B2 | 11/2017 | Rothberg et al. | |
| 10,004,462 B2 | 6/2018 | Ernst et al. | |
| 10,145,913 B2 | 12/2018 | Hugon et al. | |
| 10,145,922 B2 | 12/2018 | Rothberg et al. | |
| 10,222,434 B2 | 3/2019 | Poole et al. | |
| 10,274,561 B2 | 4/2019 | Poole et al. | |
| 10,281,540 B2 | 5/2019 | Mileski et al. | |
| 10,281,541 B2 | 5/2019 | Poole et al. | |
| 10,310,037 B2 | 6/2019 | McNulty et al. | |
| 10,335,054 B2 | 7/2019 | Wyeth et al. | |
| 10,416,264 B2 | 9/2019 | Sofka et al. | |
| 10,551,452 B2 | 2/2020 | Rearick et al. | |
| 10,591,561 B2 | 3/2020 | Sacolick et al. | |
| 10,702,212 B2 | 7/2020 | Van Helvoort | |
| 10,709,387 B2 | 7/2020 | Poole et al. | |
| 11,047,940 B2* | 6/2021 | Findeklee | G01R 33/543 |
| 11,181,600 B2 | 11/2021 | Leussler et al. | |
| 2003/0195413 A1* | 10/2003 | Rubin | A61B 5/7285 |
| | | | 600/413 |
| 2004/0030233 A1 | 2/2004 | Frazier et al. | |
| 2006/0264735 A1 | 11/2006 | Stemmer | |
| 2008/0024133 A1 | 1/2008 | Vaughan et al. | |
| 2008/0228063 A1* | 9/2008 | Turner | A61N 5/02 |
| | | | 600/411 |
| 2008/0258732 A1 | 10/2008 | Yoshizawa | |
| 2010/0106008 A1 | 4/2010 | Harvey | |
| 2010/0117650 A1* | 5/2010 | Cork | G01R 33/3621 |
| | | | 324/322 |
| 2010/0117652 A1* | 5/2010 | Cork | G01R 33/3453 |
| | | | 343/834 |
| 2010/0253345 A1* | 10/2010 | Vester | G01R 33/3621 |
| | | | 324/316 |
| 2010/0253346 A1* | 10/2010 | Hulbert | H03F 7/04 |
| | | | 324/316 |
| 2010/0253349 A1* | 10/2010 | Cork | G01R 33/3692 |
| | | | 324/123 R |
| 2010/0253350 A1* | 10/2010 | Huish | G01R 33/34007 |
| | | | 324/318 |
| 2010/0253351 A1* | 10/2010 | Huish | H01Q 21/20 |
| | | | 324/318 |
| 2010/0253352 A1* | 10/2010 | Hulbert | G01R 33/3415 |
| | | | 324/318 |
| 2010/0253353 A1* | 10/2010 | Cork | G01R 33/3692 |
| | | | 324/318 |
| 2011/0059716 A1* | 3/2011 | Cork | H03F 7/04 |
| | | | 455/330 |
| 2012/0062230 A1* | 3/2012 | Vaughan, Jr. | G01R 33/3614 |
| | | | 324/318 |
| 2012/0257806 A1 | 10/2012 | Sheltraw et al. | |
| 2013/0069652 A1* | 3/2013 | Otake | G01R 33/3664 |
| | | | 324/322 |
| 2013/0147475 A1* | 6/2013 | Yang | A61N 5/025 |
| | | | 324/309 |
| 2013/0274590 A1 | 10/2013 | Auboiroux et al. | |
| 2013/0278265 A1 | 10/2013 | Kim et al. | |
| 2014/0073908 A1 | 3/2014 | Biber | |
| 2014/0077811 A1* | 3/2014 | Lin | G01R 33/56509 |
| | | | 324/309 |
| 2014/0084924 A1 | 3/2014 | Grodzki | |
| 2014/0152309 A1 | 6/2014 | Kozlov et al. | |
| 2014/0197836 A1* | 7/2014 | Hamamura | G01R 33/44 |
| | | | 324/318 |
| 2015/0194736 A1 | 7/2015 | Diukman et al. | |
| 2015/0335268 A1* | 11/2015 | Biber | A61B 5/0816 |
| | | | 600/411 |
| 2016/0033591 A1* | 2/2016 | Leussler | G01R 33/34053 |
| | | | 324/309 |
| 2016/0038054 A1 | 2/2016 | Benner et al. | |
| 2016/0073993 A1* | 3/2016 | Ouyang | A61B 5/0035 |
| | | | 600/411 |
| 2016/0128592 A1* | 5/2016 | Rosen | A61B 5/389 |
| | | | 600/411 |
| 2016/0169999 A1 | 6/2016 | Herza et al. | |
| 2016/0209486 A1* | 7/2016 | Nisznansky | G01R 33/56509 |
| 2016/0310082 A1 | 10/2016 | Rajamani et al. | |
| 2017/0038448 A1 | 2/2017 | Beck et al. | |
| 2017/0082718 A1 | 3/2017 | Beck | |
| 2017/0146620 A1 | 5/2017 | Habara et al. | |
| 2017/0160364 A1 | 6/2017 | Fenchel et al. | |
| 2017/0160367 A1 | 6/2017 | Schröter et al. | |
| 2017/0199262 A1 | 7/2017 | Paul | |
| 2017/0214138 A1* | 7/2017 | Erturk | H01Q 1/22 |
| 2017/0303840 A1* | 10/2017 | Stadler | A61B 5/150053 |
| 2017/0307701 A1* | 10/2017 | Leussler | G01R 33/36 |
| 2018/0003791 A1 | 1/2018 | Kimmlingen et al. | |
| 2018/0045801 A1 | 2/2018 | Speier et al. | |
| 2018/0088193 A1 | 3/2018 | Rearick et al. | |
| 2018/0313919 A1* | 11/2018 | Ortiz | G01R 33/3692 |
| 2018/0317861 A1 | 11/2018 | Sun et al. | |
| 2019/0142296 A1 | 5/2019 | Woo et al. | |
| 2019/0154775 A1 | 5/2019 | Stack et al. | |
| 2019/0324098 A1 | 10/2019 | McNulty et al. | |
| 2019/0353722 A1* | 11/2019 | Stormont | G01R 33/3628 |
| 2019/0353723 A1 | 11/2019 | Dyvorne et al. | |
| 2019/0353726 A1 | 11/2019 | Poole et al. | |
| 2020/0022611 A1 | 1/2020 | Nelson et al. | |
| 2020/0022612 A1 | 1/2020 | McNulty et al. | |
| 2020/0033429 A1* | 1/2020 | Darnell | H02J 7/025 |
| 2020/0034998 A1 | 1/2020 | Schlemper et al. | |
| 2020/0041587 A1* | 2/2020 | Findeklkee | G01R 33/3628 |
| 2020/0041588 A1 | 2/2020 | O'Halloran et al. | |
| 2020/0045112 A1 | 2/2020 | Sacolick et al. | |
| 2020/0058106 A1 | 2/2020 | Lazarus et al. | |
| 2020/0072919 A1* | 3/2020 | Felder | G01R 33/34038 |
| 2020/0121263 A1 | 4/2020 | Carinci et al. | |
| 2020/0166597 A1 | 5/2020 | Speier et al. | |
| 2020/0200844 A1* | 6/2020 | Boskamp | G01R 33/4215 |
| 2020/0209334 A1 | 7/2020 | O'Halloran et al. | |
| 2020/0284863 A1* | 9/2020 | Leussler | G01R 33/34 |
| 2020/0289019 A1 | 9/2020 | Schlemper et al. | |
| 2020/0289022 A1 | 9/2020 | Coumans et al. | |
| 2020/0294229 A1 | 9/2020 | Schlemper et al. | |
| 2020/0294282 A1 | 9/2020 | Schlemper et al. | |
| 2020/0294287 A1 | 9/2020 | Schlemper et al. | |
| 2020/0337587 A1 | 10/2020 | Sacolick et al. | |
| 2020/0341082 A1* | 10/2020 | Woo | G01R 33/288 |
| 2020/0341083 A1* | 10/2020 | Ohishi | G01R 33/3692 |
| 2020/0355765 A1 | 11/2020 | Chen et al. | |
| 2021/0048498 A1 | 2/2021 | Dyvorne et al. | |
| 2021/0059555 A1 | 3/2021 | Buchwald et al. | |
| 2021/0063517 A1* | 3/2021 | Leussler | G01R 33/56563 |
| 2021/0080528 A1* | 3/2021 | Bindseil | G01R 33/3856 |
| 2021/0124001 A1* | 4/2021 | Boskamp | G01R 33/34038 |
| 2021/0124003 A1* | 4/2021 | Lazarus | G01R 33/5608 |
| 2021/0325525 A1* | 10/2021 | Biber | G01R 33/36 |
| 2022/0082642 A1* | 3/2022 | Biber | G01R 33/34038 |
| 2022/0187406 A1 | 6/2022 | Wang et al. | |
| 2022/0244334 A1 | 8/2022 | Sacolick et al. | |

OTHER PUBLICATIONS

PCT/US2020/056841, Apr. 1, 2021, International Search Report and Written Opinion.

International Search Report and Written Opinion for International Application No. PCT/US2020/056841 dated Apr. 1, 2021.

U.S. Appl. No. 17/077,882, filed Oct. 22, 2021, Boskamp et al.

PCT/US2020/056841, Feb. 8, 2021, Invitation to Pay Additional Fees.

Invitation to Pay Additional Fees for International Application No. PCT/US2020/056841 dated Feb. 8, 2021.

PCT/US2020/056841, May 5, 2022, International Preliminary Report on Patentability.

(56) References Cited

OTHER PUBLICATIONS

International Preliminary Report on Patentability for International Application No. PCT/US2020/056841 dated May 5, 2022.

* cited by examiner

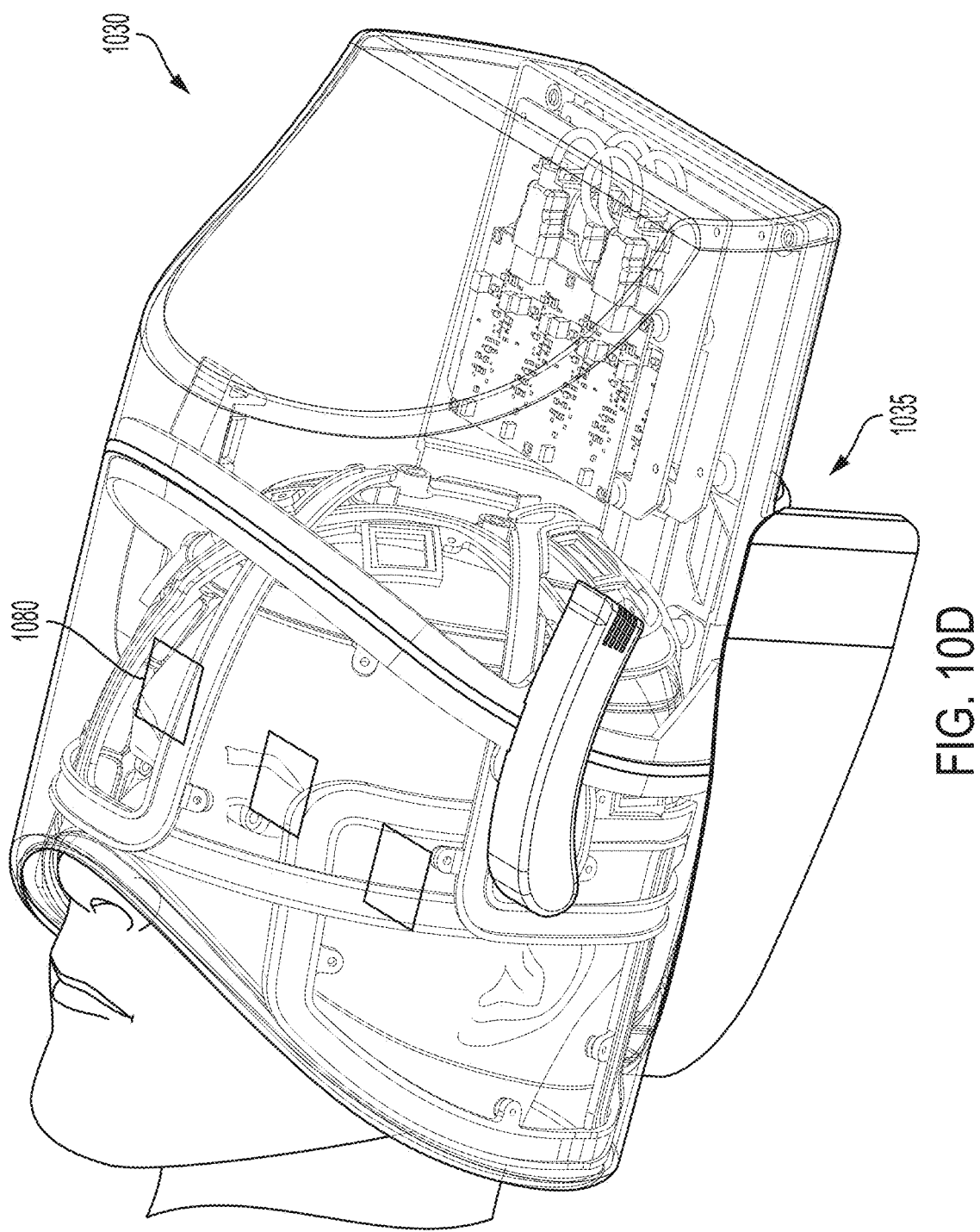

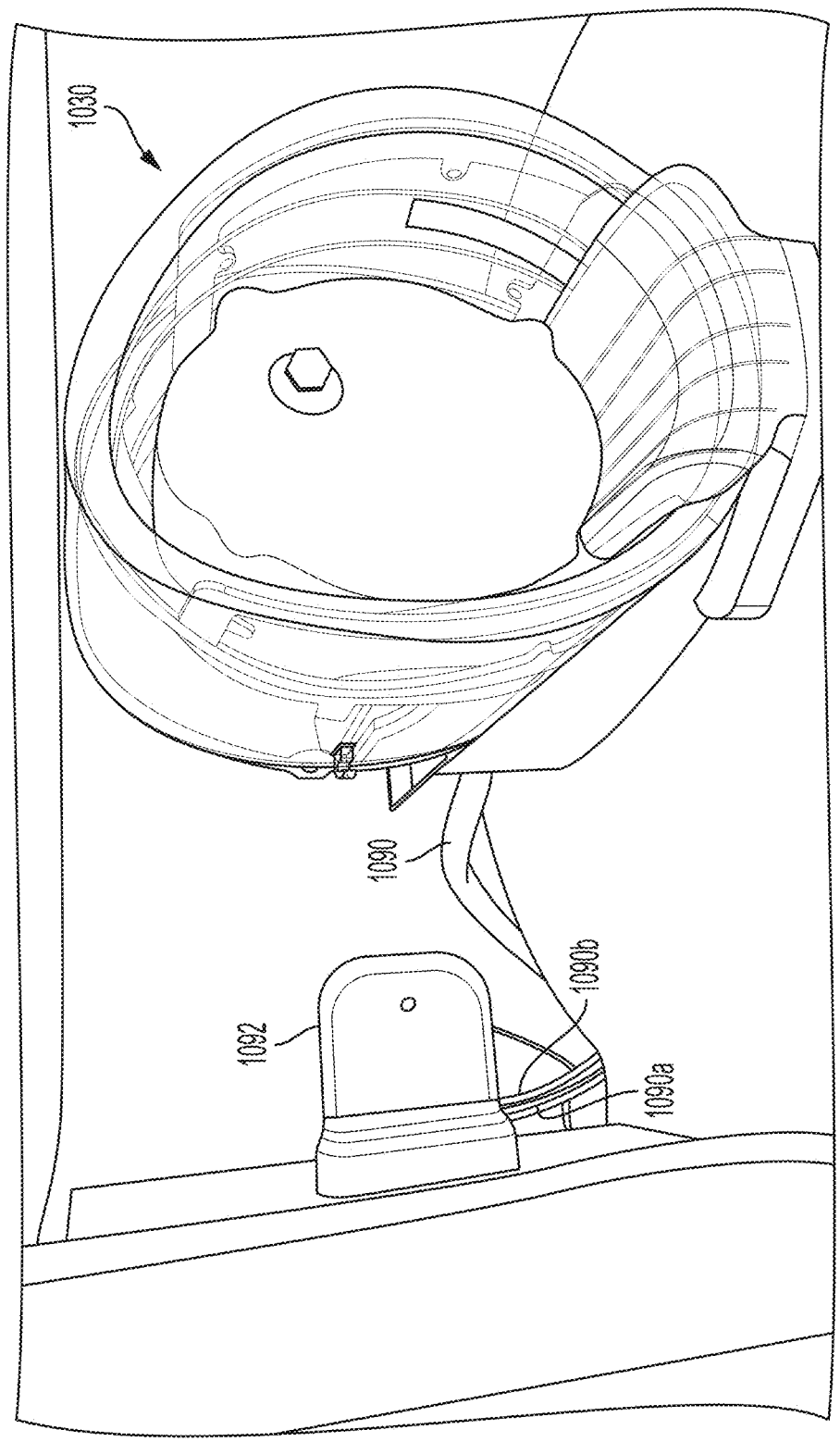

SYSTEMS AND METHODS FOR DETECTING PATIENT MOTION DURING MAGNETIC RESONANCE IMAGING

RELATED APPLICATIONS

This application claims priority under 35 U.S.C. § 119(e) to U.S. Provisional Patent Application Ser. No. 62/925,865, titled "SYSTEMS AND METHODS FOR DETECTING PATIENT MOTION DURING MAGNETIC RESONANCE IMAGING," filed on Oct. 25, 2019, which is incorporated by reference in its entirety herein.

BACKGROUND

Magnetic resonance imaging (MRI) provides an important imaging modality for numerous applications and is widely utilized in clinical and research settings to produce images of the inside of the human body. As a generality, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

SUMMARY

Some embodiments are directed to a device configured to accommodate a patient's anatomy during magnetic resonance (MR) imaging. The device comprises at least one radio frequency (RF) transmit and/or receive coil; and at least one sensor, different from the at least one RF transmit and/or receive coil, configured to be capacitively coupled to the patient during MR imaging.

Some embodiments are directed to a device configured to accommodate a patient's anatomy during MR imaging by a magnetic resonance imaging (MRI) system, the MRI system comprising at least one RF transmit and/or receive coil. The device comprises at least one RF sensor, different from the at least one RF transmit and/or receive coil of the MRI system, configured to be capacitively coupled to the patient for determining whether the patient moved during MR imaging. The device also comprises an attachment mechanism configured to couple the device with the MRI system.

Some embodiments are directed to an MRI system configured to capture an MR image. The MRI system comprises a $B_0$ magnet configured to provide at least a portion of a $B_0$ field and a device configured to accommodate a patient's anatomy during magnetic resonance (MR) imaging. The device comprises at least one RF transmit and/or receive coil and at least one sensor, different from the at least one RF transmit and/or receive coil, configured to be capacitively coupled to the patient during MR imaging.

Some embodiments are directed to an MRI system configured to capture an MR image. The MRI system comprises: a $B_0$ magnet configured to provide at least a portion of a $B_0$ field; at least one sensor and configured to be capacitively coupled to a patient during MRI; and at least one processor. The at least one processor is configured to, while the patient is positioned within the MRI system, measure a reflected signal value characteristic of a signal reflected by the at least one sensor in response to being driven by at least one RF signal; and determine, using the reflected signal value, whether the patient has moved.

In some embodiments, the at least one sensor comprises at least one RF sensor.

In some embodiments, the at least one RF sensor is configured to resonate at a frequency between 100 MHz and 250 MHz.

In some embodiments, the at least one RF sensor comprises at least one RF antenna.

In some embodiments, the at least one RF antenna comprises at least one RF dipole antenna.

In some embodiments, the at least one dipole antenna comprises four dipole antennas.

In some embodiments, the four dipole antennas are coupled to a helmet configured to accommodate a patient's head during MR imaging.

In some embodiments, the four dipole antennas are positioned on an inner surface of the helmet and arranged in two sets of two dipole antennas each, wherein: the dipole antennas of each set of two dipole antennas are disposed along a respective axis; and the patient's head is located on the respective axis between the dipole antennas of each set of two dipole antennas.

In some embodiments, the at least one dipole antenna comprises at least one inductor coupled to a lattice balun. In some embodiments, the at least one inductor is coupled to the lattice balun through at least a portion of a conductive arm of the RF dipole antenna. In some embodiments, the at least one inductor is configured to reduce the physical length of the RF dipole antenna. In some embodiments, the at least one dipole antenna comprises at least one varactor diode coupled in parallel with the at least one inductor.

In some embodiments, the at least one dipole antenna comprises at least one conductive arm, the at least one conductive arm including at least one 90-degree bend.

In some embodiments, the device is configured to accommodate a patient's foot during MR imaging.

In some embodiments, the device is configured to accommodate a patient's head during MR imaging.

In some embodiments, the device comprises a helmet. The helmet has a surface, and the at least one RF sensor is disposed on the surface.

In some embodiments, the device comprises an attachment mechanism configured to couple the device with an MR imaging system.

In some embodiments, determining whether the patient has moved comprises calculating a ratio of the reflected signal value from the at least one RF sensor to a signal value of the at least one RF signal; and comparing the calculated ratio to a threshold value.

In some embodiments, measuring the reflected signal value includes measuring a voltage of the signal reflected by the at least one RF sensor in response to being driven by at least one RF signal.

In some embodiments, the at least one sensor is calibrated prior to imaging the patient. Calibrating the at least one sensor comprises: driving the at least one sensor with a calibration RF signal, the calibration RF signal varying in frequency over time; identifying a resonant frequency of the at least one sensor; and setting a frequency of the at least one RF signal to be different from the resonant frequency and within 5% of the resonant frequency.

In some embodiments, identifying a resonant frequency of the at least one sensor comprises: measuring, for each frequency in a plurality of frequencies, a reflected signal value characteristic of a signal reflected by the at least one sensor when driven by a signal having the frequency; and identifying the resonant frequency of the at least one sensor to be that frequency from among the plurality of frequencies for which a smallest respective reflected signal value was measured.

In some embodiments, the at least one sensor comprises a first sensor and a second sensor, the first sensor being disposed opposite the second sensor such that the patient is positioned between the first sensor and the second sensor. The at least one processor is further configured to, while the patient is positioned within the MRI system, measure a first reflected signal value characteristic of a signal reflected by the first sensor in response to being driven by a first RF signal; measure a second reflected signal value characteristic of a signal reflected by the second sensor in response to being driven by a second RF signal different from the first RF signal; and determine, using the first and second reflected signal values, whether the patient has moved.

In some embodiments, the MRI system further comprises a radio frequency (RF) coil configured to provide a $B_1$ field and is different from the at least one sensor.

Some embodiments are directed to a method. The method comprises, while a patient is positioned within a magnetic resonance imaging (MRI) system: measuring a reflected signal value characteristic of a signal reflected by at least one sensor in response to being driven by at least one RF signal; and determining, using the reflected signal value, whether the patient has moved.

Some embodiments are directed to at least one non-transitory computer-readable storage medium storing processor-executable instructions that, when executed by a magnetic resonance imaging (MRI) system, cause the MRI system to perform a method. The method comprises using a processor configured to, while a patient is positioned within the MRI system: measure a reflected signal value characteristic of a signal reflected by at least one sensor in response to being driven by at least one RF signal; and determine, using the reflected signal value, whether the patient has moved.

In some embodiments, the at least one RF signal comprises a frequency between 100 MHz and 250 MHz.

In some embodiments, determining whether the patient has moved comprises calculating a ratio of the reflected signal value from the at least one sensor to a signal value of the at least one RF signal; and comparing the calculated ratio to a threshold value.

In some embodiments, the method further comprises calibrating the at least one sensor. Calibrating the at least one sensor comprises: driving the at least one sensor with a calibration RF signal, the calibration RF signal varying in frequency over time; identifying a resonant frequency of the at least one sensor; and setting a frequency of the at least one RF signal to be different from the resonant frequency and within 5% of the resonant frequency.

In some embodiments, identifying the resonant frequency of the at least one sensor comprises: measuring, for each frequency in a plurality of frequencies, a reflected signal value characteristic of a signal reflected by the at least one sensor when driven by a signal having the frequency; and identifying the resonant frequency of the at least one sensor to be that frequency from among the plurality of frequencies for which a smallest respective reflected signal value was measured.

In some embodiments, measuring the reflected signal value includes measuring a voltage of the signal reflected by the at least one RF sensor in response to being driven by at least one RF signal.

In some embodiments, the method further comprises modifying how magnetic resonance (MR) data is acquired and/or used when it is determined that the patient has moved.

In some embodiments, modifying how MR data is acquired and/or used comprises discarding MR data collected during a time period during which the patient has moved.

In some embodiments, modifying how MR data is acquired and/or used comprises, after determining that the patient has moved, grouping the MR data into first MR data collected prior to when the patient has moved and second MR data collected after the patient has moved and generating an MR image based on the first MR data and the second MR data.

In some embodiments, modifying how MR data is acquired and/or used comprises discarding an MR image formed using MR data collected during a time period during which the patient has moved.

In some embodiments, modifying how MR data is acquired and/or used comprises correcting MR data collected during a time period during which the patient has moved.

In some embodiments, correcting the MR data comprises one or more of smoothing at least some of the MR data, rejecting at least some of the MR data, and/or interpolating at least some of the MR data.

In some embodiments, modifying how MR data is acquired and/or used comprises obtaining additional MR data to replace MR data collected during a time period during which the patient has moved.

In some embodiments, obtaining additional MR data comprises modifying a pulse sequence being used by the MRI system to obtain additional MR data at points in k-space that were obtained during a time period in which the patient has moved.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 10D illustrates another view of a helmet including a patient and sensors for detecting motion by the patient during imaging, in accordance with some embodiments of the technology described herein.

FIG. 10F illustrates another view of a helmet disposed within an MRI system, in accordance with some embodiments of the technology described herein.

DETAILED DESCRIPTION

Figure 1:
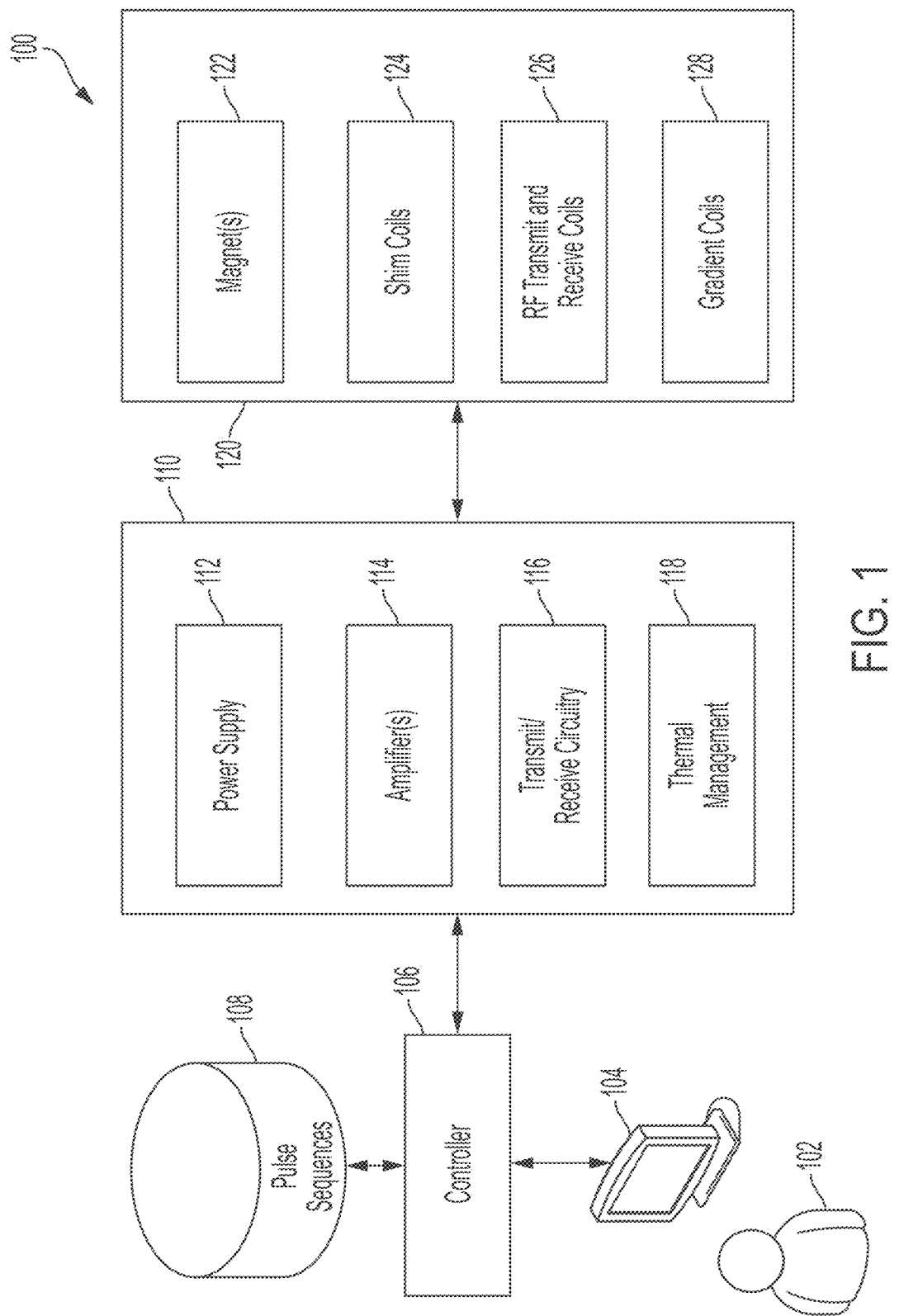
FIG. 1 illustrates exemplary components of a magnetic resonance imaging system, in accordance with some embodiments of the technology described herein.

The quality of acquired magnetic resonance (MR) images may be significantly impacted by a patient's motion during an MRI procedure, as movement by the patient during imaging may generate artefacts in the resulting MR images. Conventional approaches to mitigating this problem involve restraining patients in one or more directions of motion to reduce the introduction of artefacts into a resulting MR image. However, such restraints are uncomfortable for a patient or may cause a patient to feel claustrophobic during an MR imaging procedure.

Conventional methods of minimizing noise due to a patient's motion can be improved by detecting the patient's position and/or motion during MR imaging and using instances of detected changes in position to correct the resulting MR images. However, many off-the-shelf motion detectors do not function well when placed within the magnetic fields required for MRI and/or the detectors interfere with proper functioning of the MRI system. Other methods of patient motion detection rely on imaging the patient with an optical camera system while the patient is positioned within the MRI system, but such optical camera systems can be expensive to implement and too slow to detect the patient's motion instantaneously.

The inventors have appreciated that the resonant frequency of a sensor (e.g., an RF sensor such as an RF antenna) may change when in the presence of a subject (e.g., a patient) due to the parasitic capacitance between the sensor and the subject. For example, the resonant frequency of the sensor may decrease as the distance between the sensor and the patient decreases. Accordingly, the inventors have developed a system for detecting position and/or motion of a patient during an MR imaging procedure using at least one sensor configured to capacitively couple with the patient.

The inventors have recognized that detecting a resonant frequency shift of a sensor to detect patient motion may require bulky and costly electronics and may provide less sensitivity. For example, monitoring the sensor's resonant frequency could be achieved by performing a full frequency sweep and detecting the frequency which induces that maximum current in the sensor. However, performing such a frequency sweep requires additional electronics, which is expensive. Moreover, a frequency sweep may be time consuming to execute. To avoid these problems, the inventors have developed a technique for detecting patient position and/or motion by monitoring a reflected power at a set frequency from the sensor rather than detecting a change in the sensor's resonant frequency. The set frequency may be determined based on the resonant frequency of the sensor and set to a frequency such that the sensitivity of the sensor is increased (e.g., to a frequency such that the reflection curve has a maximum slope).

The inventors have developed a device for detecting motion of a patient while the patient is positioned within the MRI system. In some embodiments, the device includes at least one sensor (e.g., one or more RF antennas, for example, multiple RF dipole antennas) configured to be capacitively coupled to the patient during MR imaging. In some embodiments, while the patient remains positioned within the MRI system, the device may be configured to drive the at least one sensor with at least one radio frequency (RF) signal and measure a reflected signal value from the at least one sensor. The reflected signal value may be characteristic of a signal reflected by the at least one sensor in response to the at least one RF signal. For example, the reflected signal value may be a voltage. In some embodiments, a reflection coefficient calculated from the reflected signal value that is below a threshold reflection coefficient value may be indicative of a patient's motion. The threshold reflection coefficient value may be determined based on a previously measured reflection coefficient value (e.g., the threshold reflection coefficient value may be a previously measured reflection coefficient value plus and/or minus a percentage value indicative of noise). Accordingly, the reflected signal value and/or reflection coefficient obtained by using the device may be used to determine whether the patient has moved.

In some embodiments, a calibration procedure may be used to increase sensitivity of a sensor to the parasitic capacitance of the patient. The sensor may be most sensitive to parasitic capacitance when driven by at least one RF signal having a frequency different from the sensor's resonant frequency (e.g., within 5% of the sensor's resonant frequency). In some embodiments, calibrating the sensor may include driving the sensor with a calibration RF signal whose frequency varies over time, identifying a resonant frequency of the sensor, and setting a driving frequency to be used for driving the sensor to be either the sensor's resonant frequency or within 5% of its identified resonant frequency. As described herein, the driving frequency may be set to a frequency such that the sensitivity of the sensor is increased (e.g., to a frequency such that the reflection curve has a maximum slope).

In some embodiments, identifying the resonant frequency of a sensor may include measuring a reflected signal value from the sensor for each of multiple frequencies (e.g., of the calibration RF signal). In some embodiments, the resonant frequency of the sensor may be identified from among the multiple frequencies by identifying the frequency for which a smallest respective reflected signal value was measured.

In some embodiments, one or more sensors may be employed to measure patient movement and the one or more sensors may include at least one RF sensor (e.g., an RF antenna). In some embodiments, the sensor(s) may include at least one dipole antenna. In some embodiments, the dipole antenna may include at least one inductor coupled to a lattice balun. In some embodiments, each sensor or sensors may be configured to resonate at a frequency between 100 MHz and 250 MHz.

In some embodiments, the device may be configured to accommodate a patient's anatomy (e.g., the patient's head, leg, arm, foot, or other appendage) during an MR imaging procedure. For example, the device may include a helmet to accommodate the patient's head. In some embodiments, the device may include an attachment mechanism configured to securely mechanically couple the device to the MRI system, further reducing patient and/or device motion during MR imaging and reducing noise in resulting MR images.

In some embodiments, the sensor(s) used to detect patient motion may be coupled to a surface of a helmet configured to accommodate the patient's head. To enable motion detection in multiple directions, in some embodiments, multiple (e.g., four) sensors may be coupled to the device (e.g., to a surface of the helmet). In some embodiments, the four sensors may be grouped in pairs such that the patient's anatomy (e.g., the patient's head) is positioned between two sensors of each pair of sensors. Positioning the patient's anatomy between two sensors may maintain the patient's position within range of at least one sensor at all times and may allow for the detection of the patient's motion in both directions along an axis connecting the two sensors. When multiple pairs of sensors are used, the pairs of sensors may be disposed along different axes (e.g., perpendicular axes) to detect motion of the patient in both directions along multiple axes.

In some embodiments, the device may further include at least one RF transmit and/or receive coil configured to provide a B1 magnetic field during MR imaging and/or detect MR signals emitted by the subject. In some embodiments, the at least one sensor is different from the at least one RF transmit and/or receive coil. To prevent electromagnetic interference between the at least one sensor and the at least one RF transmit and/or receive coil, the at least one sensor may be configured to resonate at a different frequency than the RF transmit and/or receive coil. In some embodiments, where the at least one sensor includes two or more sensors, each of the two or more sensors may be configured to resonate at different frequencies from the RF transmit and/or receive coil as well as the other sensors of the two or more sensors.

In some embodiments, detecting a patient's motion during an MR imaging procedure may enable the MRI system and/or device to modify how MR data is acquired and/or used to reduce artifacts in resulting MR images. For example, in some embodiments, MR data collected during a time period during which the patient has moved (and/or MR images determined from such data) may be discarded. In some embodiments, MR data collected (and/or MR images determined from such data) during a time period during which the patient has moved may be corrected. Correcting MR data and/or images collected during a time period during which the patient has moved may include smoothing at least some of the MR data and/or images, rejecting at least some of the MR data and/or images, and/or interpolating at least some of the MR data and/or images.

In some embodiments, additional MR data may be acquired to replace MR data collected during a time period during which the patient has moved. For example, in some embodiments, obtaining additional MR data may include modifying a pulse sequence being used by the MRI system to obtain additional MR data at points in k-space that were obtained during a time period in which the patient has moved.

In some embodiments, correcting MR data may include generating MR images from spatial frequency data obtained by the MRI system in circumstances when the patient moves during imaging. In some embodiments, generating the MR images involves dividing the spatial frequency data into two sets of spatial frequency data, corresponding to two positions of the patient during imaging, with spatial frequency data collected during the patient's movement between the positions being discarded. Dividing the spatial frequency data into two sets of spatial frequency data may be performed based on additional information obtained by one or more sensors configured to detect and/or track motion of the patient being imaged. For example, one or more RF sensors as described herein may be used to obtain information indicating when a patient has moved during MR imaging and/or how the position of the patient has changed during MR imaging. In some embodiments, the first spatial frequency data may be identified as the spatial frequency data collected prior to the patient's motion (e.g., when the patient is in a first position) and the second spatial frequency data may be identified as the spatial frequency data collected subsequent to the patient's motion (e.g., when the patient is in a second position). In some embodiments, the spatial frequency data collected during the patient's motion (e.g., from the first position to the second position) may be removed.

In turn, the sets of spatial frequency data are used to estimate a transformation (e.g., a rigid transformation comprising a rotation and a translation) representing the patient's motion, and the transformation may be used to correct the spatial frequency data for the effect of motion. It should be appreciated that the spatial frequency data may be divided into any suitable number of sets of spatial frequency data corresponding to any suitable number of positions of the patient during MR imaging (e.g., 3, 4, 5, 6, etc.), and pairwise rigid transformations may be estimated therebetween for correcting spatial frequency data for the patient's motion, as aspects of the technology described herein are not limited in this respect.

Following below are more detailed descriptions of various concepts related to, and embodiments of, techniques for automatic messaging. It should be appreciated that various aspects described herein may be implemented in any of numerous ways. Examples of specific implementations are provided herein for illustrative purposes only. In addition, the various aspects described in the embodiments below may be used alone or in any combination and are not limited to the combinations explicitly described herein.

FIG. 1 is a block diagram of typical components of an MRI system 100. In the illustrative example of FIG. 1, MRI system 100 comprises computing device 104, controller 106, pulse sequences store 108, power management system 110, and magnetics components 120. It should be appreciated that system 100 is illustrative and that an MRI system may have one or more other components of any suitable type in addition to or instead of the components illustrated in FIG. 1. However, an MRI system will generally include these high-level components, though the implementation of these components for a particular MRI system may differ. It may be appreciated that the techniques described herein for detecting patient motion may be used with any suitable type of MRI systems including high-field MRI systems, low-field MRI systems, and ultra-low field MRI systems. For example, the techniques described herein may be used with any of the MRI systems described herein and/or as described in U.S. Patent Application Publication No. 2018/143,280 filed Jun. 30, 2017, and titled "Low-Field Magnetic Resonance Imaging Methods and Apparatus," which is incorporated by reference herein in its entirety.

As illustrated in FIG. 1, magnetics components 120 comprise $B_0$ magnet 122, shim coils 124, radio frequency (RF) transmit and receive coils 126, and gradient coils 128. $B_0$ magnets 122 may be used to generate the main magnetic field $B_0$. $B_0$ magnets 122 may be any suitable type or combination of magnetics components that can generate a desired main magnetic $B_0$ field. In some embodiments, $B_0$ magnets 122 may be a permanent magnet, an electromagnet, a superconducting magnet, or a hybrid magnet comprising one or more permanent magnets and one or more electromagnets and/or one or more superconducting magnets. In some embodiments, $B_0$ magnets 122 may be configured to generate a $B_0$ magnetic field having a field strength that is less than or equal to 0.2 T or within a range from 50 mT to 0.1 T.

For example, in some embodiments, $B_0$ magnets 122 may include a first and second $B_0$ magnet, each of the first and second $B_0$ magnet including permanent magnet blocks arranged in concentric rings about a common center. The first and second $B_0$ magnet may be arranged in a bi-planar configuration such that the imaging region is located between the first and second $B_0$ magnets. In some embodiments, the first and second $B_0$ magnets may each be coupled to and supported by a ferromagnetic yoke configured to capture and direct magnetic flux from the first and second $B_0$ magnets. Additional details of such embodiments are described in U.S. Pat. No. 10,545,207 titled "Low-Field magnetic Resonance Imaging Methods and Apparatus" filed on Apr. 18, 2018, which is incorporated by reference herein in its entirety.

Gradient coils 128 may be arranged to provide gradient fields and, for example, may be arranged to generate gradients in the $B_0$ field in three substantially orthogonal directions (X, Y, Z). Gradient coils 128 may be configured to encode emitted MR signals by systematically varying the $B_0$ field (the $B_0$ field generated by magnet 122 and/or shim coils 124) to encode the spatial location of received MR signals as a function of frequency or phase. For example, gradient coils 128 may be configured to vary frequency or phase as a linear function of spatial location along a particular direction, although more complex spatial encoding profiles may also be provided by using nonlinear gradient coils. In some embodiments, gradient coils 128 may be implemented using laminate panels (e.g., printed circuit boards). Examples of such gradient coils are described in U.S. Pat. No. 9,817,093 titled "Low Field Magnetic Resonance Imaging Methods and Apparatus" filed on Sep. 4, 2015, which is incorporated by reference herein in its entirety.

MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein. In FIG. 1, RF transmit and receive circuitry 126 comprises one or more transmit coils that may be used to generate RF pulses to induce an oscillating magnetic field $B_1$. The transmit coil(s) may be configured to generate any suitable types of RF pulses. The transmit and receive circuitry 116 may include additional electronic components of the transmit and receive chains, as described in U.S. Patent Application Publication No. 2019/0353723 titled "Radio-Frequency Coil Signal Chain for a Low-Field MRI System" and filed on May 21, 2019, which is hereby incorporated by reference in its entirety.

Power management system 110 includes electronics to provide operating power to one or more components of the low-field MRI system 100. For example, power management system 110 may include one or more power supplies, gradient power components, transmit coil components, and/or any other suitable power electronics needed to provide suitable operating power to energize and operate components of MRI system 100. As illustrated in FIG. 1, power management system 110 comprises power supply 112, power component(s) 114, transmit/receive circuitry 116, and thermal management components 118 (e.g., cryogenic cooling equipment for superconducting magnets). Power supply 112 includes electronics to provide operating power to magnetic components 120 of the MRI system 100. For example, power supply 112 may include electronics to provide operating power to one or more $B_0$ coils (e.g., $B_0$ magnet 122) to produce the main magnetic field for the low-field MRI system.

Amplifier(s) 114 may include one or more RF receive (Rx) pre-amplifiers that amplify MR signals detected by one or more RF receive coils (e.g., coils 126), one or more RF transmit (Tx) power components configured to provide power to one or more RF transmit coils (e.g., coils 126), one or more gradient power components configured to provide power to one or more gradient coils (e.g., gradient coils 128), and one or more shim power components configured to provide power to one or more shim coils (e.g., shim coils 124). Transmit/receive circuitry 116 may be configured to select whether RF transmit coils or RF receive coils are being operated (e.g., using a switch or switches).

As illustrated in FIG. 1, MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence (e.g., parameters for operating the RF transmit and receive coils 126, parameters for operating gradient coils 128, etc.). As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

Figure 2A:
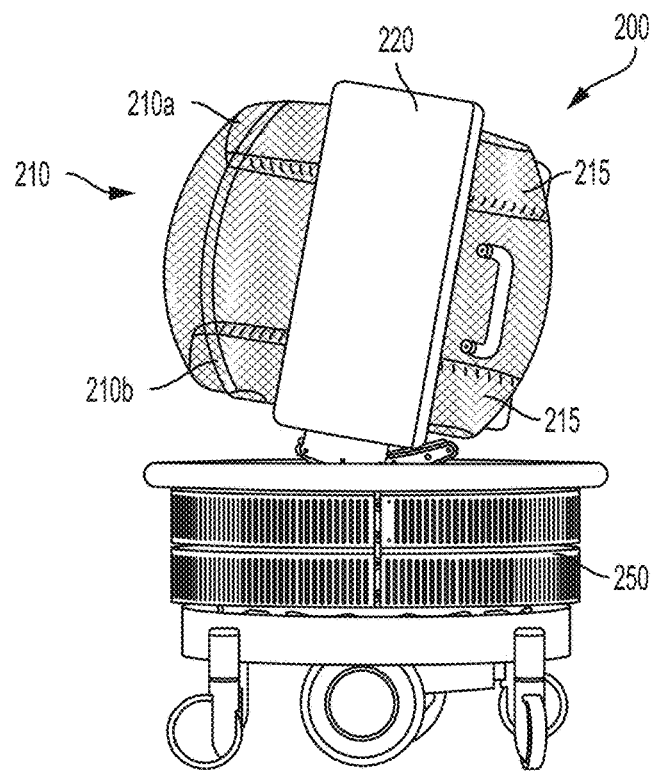
FIGS. 2A and 2B illustrate views of a portable MRI system, in accordance with some embodiments of the technology described herein.
Figure 2B:
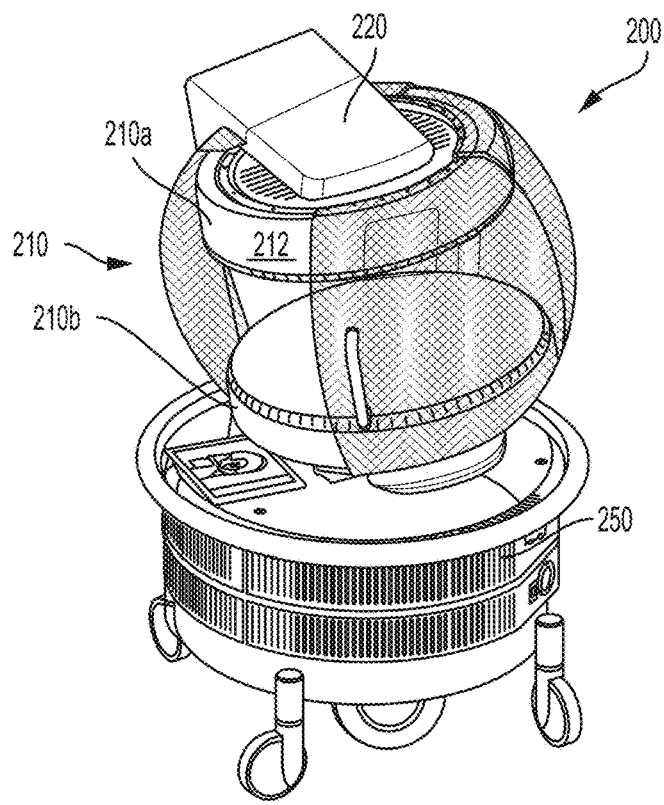

FIGS. 2A and 2B illustrate views of a portable MRI system, in accordance with some embodiments. Portable MRI system 200 comprises a $B_0$ magnet 210 formed in part by an upper magnet 210a and a lower magnet 210b having a yoke 220 coupled thereto to increase the flux density within the imaging region. The $B_0$ magnet 210 may be housed in magnet housing 212 along with gradient coils 215 (e.g., any of the gradient coils described in U.S. Pat. No. 9,817,093, titled "Low Field Magnetic Resonance Imaging Methods and Apparatus" and filed on Sep. 4, 2015, which is herein incorporated by reference in its entirety). According to some embodiments, $B_0$ magnet 210 comprises an electromagnet. According to some embodiments, $B_0$ magnet 210 comprises a permanent magnet.

Figure 3:
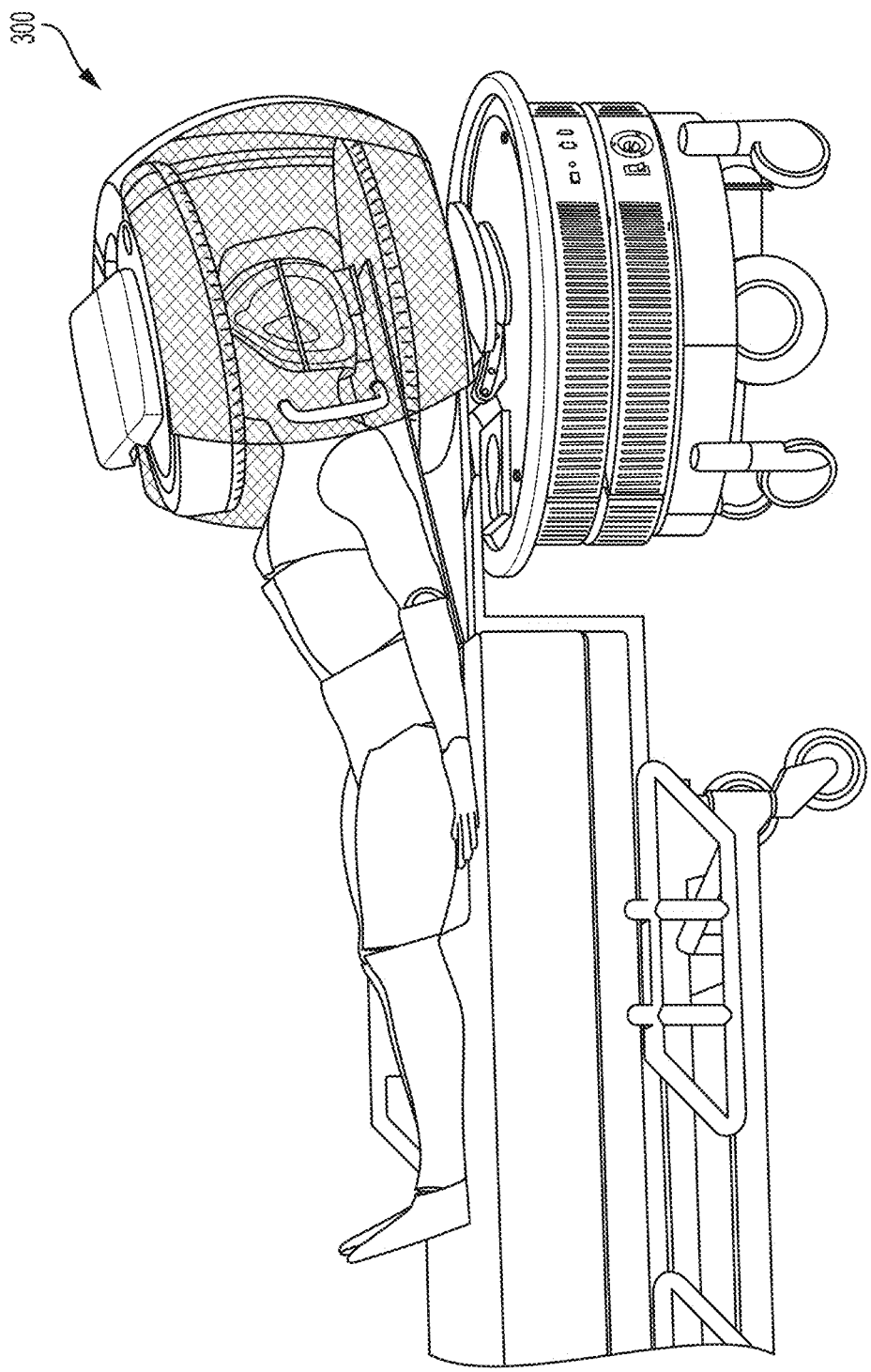
FIG. 3 illustrates a portable MRI system performing a scan of a patient's head, in accordance with some embodiments of the technology described herein.

Portable MRI system 200 further comprises a base 250 housing the electronics needed to operate the MRI system. For example, base 250 may house electronics including power components configured to operate the MRI system using mains electricity (e.g., via a connection to a standard wall outlet and/or a large appliance outlet). Accordingly, portable MRI system 200 can be brought to the patient and plugged into a wall outlet in the vicinity. In this manner, portable MRI system 200 can be transported to the patient and maneuvered to the bedside to perform imaging, as illustrated in FIG. 3. For example, FIG. 3 illustrates a portable MRI system 300 that has been transported to a patient's bedside to perform a brain scan.

Figure 4A:
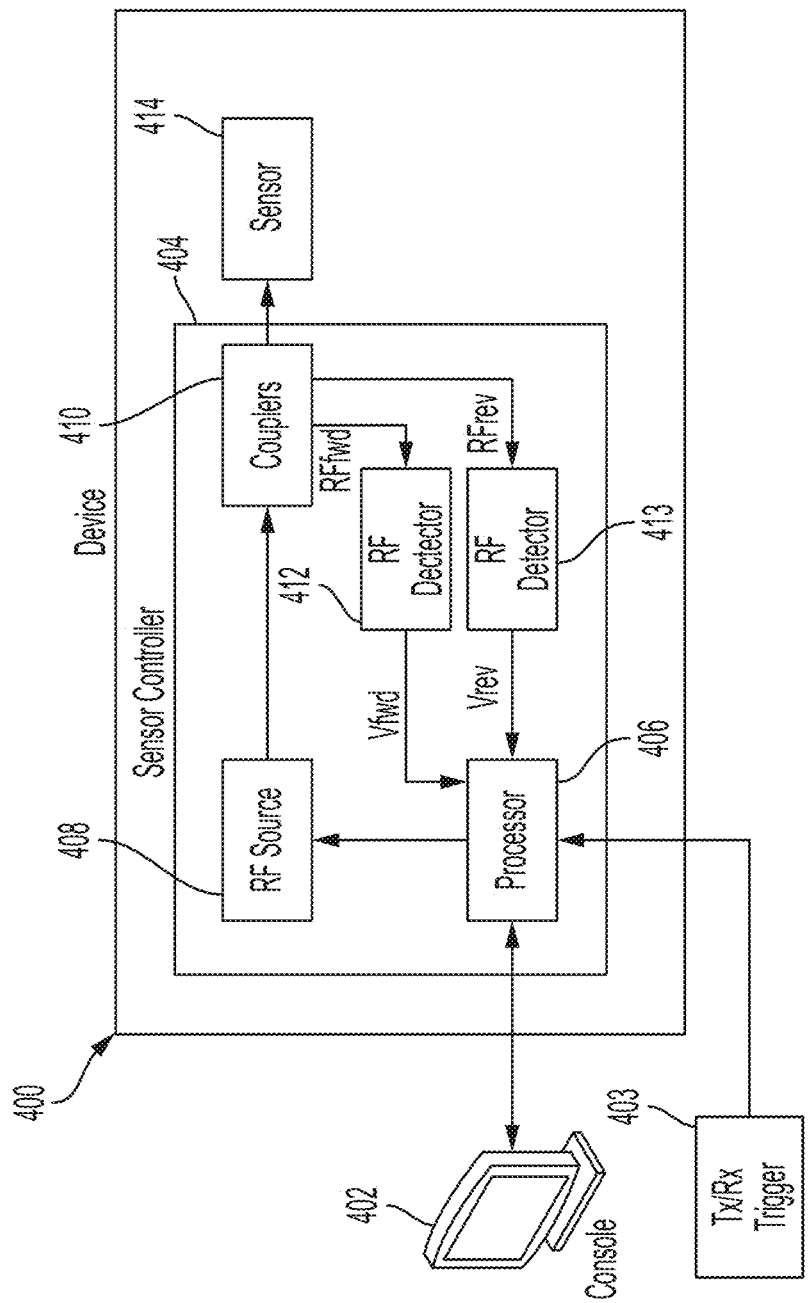
FIG. 4A illustrates exemplary components of a device for detecting motion of a patient, in accordance with some embodiments of the technology described herein.

FIG. 4A illustrates a block diagram representing components of a device 400 configured to detect position and/or motion of a patient positioned within an MRI system, in accordance with some embodiments of the technology described herein. Device 400 may be communicatively coupled with a console 402 of an MRI system (e.g., one or more of the MRI systems 200 and/or 300 described in connection with FIGS. 2A-2B and 3). Console 402 may be communicatively coupled with sensor controller 404 and sensor 414. It should be appreciated that while only one sensor 414 is depicted in FIG. 4A, in some embodiments multiple sensors 414 (e.g., two, four, and/or six sensors) may be coupled to sensor controller 404. It should further be appreciated that, while not shown in the example of FIG. 4A, additional DC components may be included in device 400. For example, in some embodiments, additional filters (e.g., bandpass filters), bias tees, analog-to-digital converters (ADCs), and/or digital-to-analog converters (DACs) may be included in device 400.

In some embodiments, sensor 414 may be configured to be capacitively coupled with a patient through a parasitic capacitance. In some embodiments, sensor 414 may be an RF sensor configured to resonate at an RF frequency. In some embodiments, sensor 414 may be an RF antenna (e.g., a loop antenna, a bowtie antenna, a dipole antenna, or any other RF antenna configured to resonate at a desired resonant frequency). In some embodiments, sensor 414 may be a dipole antenna, as described herein including with reference to FIGS. 6 and 7 herein. In some embodiments, sensor 414 may have a resonant frequency between 100 MHz and 250 MHz.

In some embodiments, sensor controller 404 may include several components configured to drive sensor 414 with an RF signal and to measure a value of a reflected signal from sensor 414 in response to the RF signal. The value of the reflected signal from sensor 414 may indicate a degree of capacitive coupling between the sensor 414 and a patient positioned within the MRI system. The capacitive coupling between the sensor 414 and the patient may change in response to a change in the distance between the sensor 414 and the patient (e.g., as the patient moves toward or away from the sensor 414), as is illustrated in FIG. 5.

Figure 5:
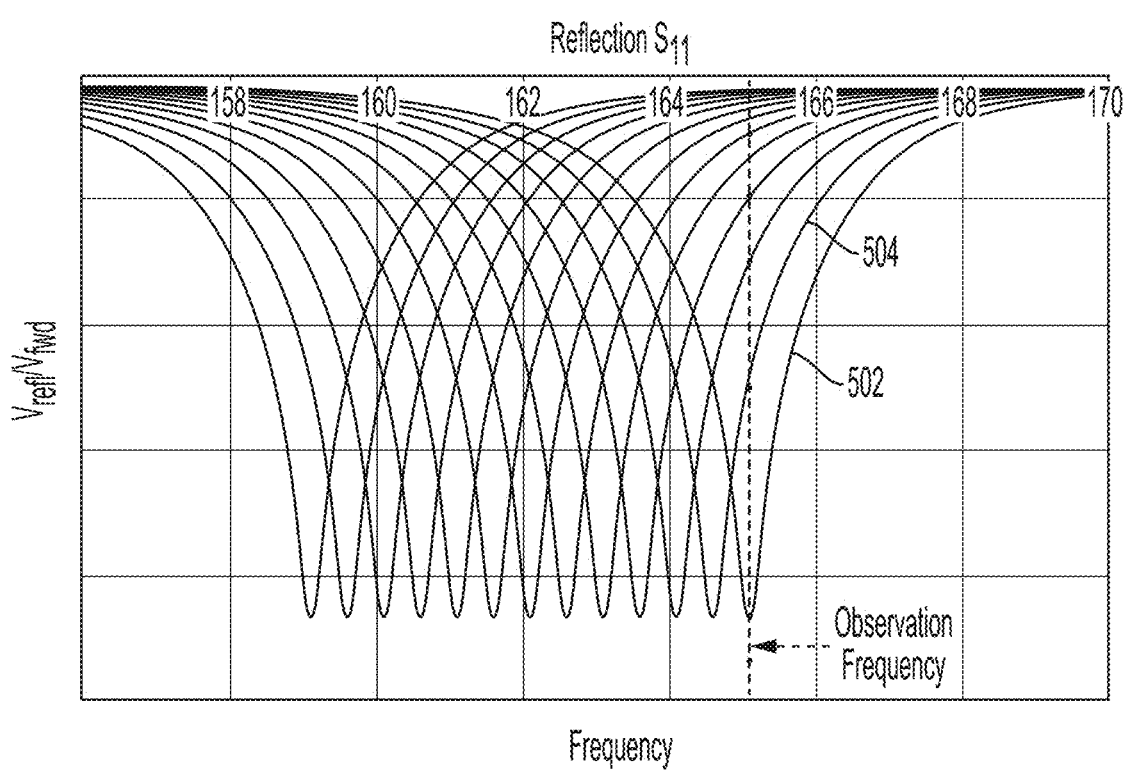
FIG. 5 illustrates a simulated reflection coefficient as a function of frequency for different capacitive loads, in accordance with some embodiments of the technology described herein.

FIG. 5 shows simulated values of a ratio of reflected signal, $V_{refl}$, (e.g., voltage of the reflected signal from sensor 414) to an input signal, $V_{fwd}$, (e.g., voltage of the RF signal from RF source 408) as a function of frequency for different capacitive loads on a sensor, in accordance with some embodiments. As the capacitive load is increased (e.g., a patient is moved closer to the sensor in the helmet on the patient's head), the resonant frequency of the sensor may decrease. For example, curve 502 has a higher resonant frequency (represented by a minimum value of $V_{refl}/V_{fwd}$) than curve 504 because curve 502 was simulated with a lower capacitive load than curve 504.

In some embodiments, device 400 may be configured to monitor an observation frequency corresponding to a resonant frequency of the unloaded sensor 414 (e.g., when the patient is not positioned within the MRI system, curve 502). When a patient is positioned within the MRI system (e.g., curve 504), the frequency response of the sensor 414 will decrease. The reflection coefficient, $V_{refl}/V_{fwd}$, measured at the observation frequency may accordingly change as a function of patient position. The measured reflection coefficient $V_{refl}/V_{fwd}$ may be compared to a threshold value to determine whether the patient's motion is to a degree that may affect accurate acquisition of MR data and/or to determine whether the acquired MR data is to be post-processed to compensate for the motion. The threshold value may be determined based on a previous measured reflection coefficient. For example, the threshold value may be determined based on adding and/or subtracting a percentage of a previously measured reflection coefficient to the previously measured reflection coefficient (e.g., the threshold value may be a previously measured reflection coefficient ±5%, ±10%, and/or ±20%). The percentage of the previously measured reflection coefficient may be chosen to be representative of acceptable noise.

Returning to FIG. 4A, in some embodiments, sensor controller 404 may include a processor 406. In some embodiments, the processor 406 may be a programmable system-on-a-chip (PSoC). Processor 406 may be communicatively coupled to console 402 (e.g., through serial communications). Processor 406 may receive instructions from console 402 (e.g., to initiate calibration of sensor 414, to measure a reflected power value from sensor 414). In some embodiments, processor 406 may send measurements from sensor 414 to console 402 for use in MR image reconstruction. Processor 406 may send data from sensor 414 to console 402 after (e.g., in response to) receiving it, without buffering for subsequent communication to maintain synchrony with the MRI system clock and to mitigate errors in the data stream from processor 406. In other embodiments, data may be buffered and sent in packets. The packets may be sent at time intervals of less than 100 ms in width.

In some embodiments, console 402 may include software configured to use the data sent by processor 406 from sensor 414 to aid in reconstruction of MR images from the MRI system. In some embodiments, the software may be configured to compensate for patient motion by rejecting MR data acquired during a time period during which the patient has moved. Alternatively or additionally, the software may compensate for patient motion by, after rejecting some MR data, smoothing and/or interpolating the remaining MR data to compensate for the removal of some MR data. In some embodiments, the software may compensate for patient motion by sending instructions to the MRI system to acquire additional MR data to replace MR data acquired during a time period during which the patient has moved. For example, in some embodiments obtaining additional MR data may include modifying a pulse sequence for the RF transmit and receive coils of the MRI system to obtain additional MR data at points in k-space that were initially acquired during a time period in which patient motion was detected.

In some embodiments, processor 406 may be communicatively coupled with an RF source 408. For example, processor 406 may be communicatively coupled with RF source 408 through an I2C bus. RF source 408 may be, for example, a programmable RF oscillator (e.g., Silicon Labs' Si514 frequency general purpose oscillator). RF source 408 may output an RF signal that was digitally synthesized by processor 406.

In some embodiments, RF source 408 may output an RF signal to couplers 410, which may couple with sensor 414. Couplers 410 may be, for example, bi-directional couplers (e.g., ADCB-20-82+ SMT bi-directional couplers by Mini-Circuits). Couplers 410 may couple the output RF signal from RF source 408 to sensor 414. Additionally, in some embodiments, couplers 410 may couple forward power from RF source 408 to RF detector 412 and reflected power from sensor 414 to RF detector 413. For example, couplers 410 may additionally couple the output RF signal from RF source 408 to RF detector 412 to monitor the forward power of the output RF signal from RF source 408. Monitoring the forward power of the RF source 408 may mitigate issues such as drift in the RF source power. Additionally, couplers 410 may couple the reflected signal from sensor 414 to RF detector 413 to monitor the reflected power. It should be appreciated that while the example of FIG. 4A shows two RF detectors 412 and 413, in some embodiments, only a single RF detector may be present (e.g., either RF detector 412 or RF detector 413).

In some embodiments, RF detectors 412 and 413 may convert a magnitude of the received waveform to a root mean square (RMS) voltage value. For example, RF detector 412 may convert a magnitude of the power of the output RF signal to an RMS value representing the forward power value from RF source 408. Additionally, for example, RF detector 413 may convert a magnitude of the power of the reflected signal from sensor 414 to an RMS value representing the reflected power value from sensor 414. The RMS values from either RF detector 412 or 413 may be digitized with a finite number of bits of resolution (e.g., 12 bits of resolution). In some embodiments, detectors 412 may be diode detectors, linear envelope detectors, and/or logarithmic power detectors. In some embodiments, detectors 412 may be, for example, LT5581 series RF detectors by Analog Devices Inc.

In some embodiments, the digitized RMS values may be sent from detectors 412 to processor 406. Processor 406 may organize the digitized RMS values into data packets and transmit the data packets to console 402 of the MRI system. In some embodiments, processor 406 may send data packets to console 402 in response to signals from Tx/Rx trigger 403. Signals from Tx/Rx trigger 403 may indicate Tx/Rx cycles of the MRI system, thereby maintaining synchronicity between device 400 and each Tx/Rx cycle of the MRI system.

In some embodiments, prior to positioning the patient within the MRI system, sensor 414 may be calibrated. To calibrate sensor 414, its resonant frequency may be determined in order to determine a value of the output RF signal from RF source 408 which may increase the sensitivity of sensor 414. For example, setting the frequency of RF source 408 to be different from the resonant frequency of sensor 414 but within 5% of the resonant frequency may maximize the sensitivity of sensor 414.

In some embodiments, setting the frequency of RF source 408 to be different from the resonant frequency of sensor 414 may involve setting the frequency of the RF source 408 to be a frequency at which the reflection curve of sensor 414 has a maximum slope. Accordingly, the frequency of RF source 408 may depend on the Q factor of the sensor 414. For example, the sensor may be configured to have a Q factor of 20 and to resonate at 176 MHz. The frequency of RF source 408 may be set to be at the steepest portion of the reflection curve of the sensor, or at 176.3 MHz, which is 0.17% higher than the resonant frequency 176 MHz.

In some embodiments, during a calibration step, processor 406 may control RF source 408 to output an RF signal with a varying frequency. As the frequency of the RF signal output by RF source 408 is varied, processor 406 may monitor the reflected power from sensor 414. When the output RF signal reaches the resonant frequency of sensor 414, a maximum amount of the RF signal from RF source 408 may be delivered to sensor 414, and the measured reflected signal value from sensor 414 may be at a minimum. Processor 406 may determine which output frequency from RF source 408 results in a minimum reflected signal value from sensor 414. Processor 406 may then set the frequency of RF source 408 to be different from the resonant frequency of sensor 414 but within 5% of the resonant frequency of sensor 414.

Figure 4B:
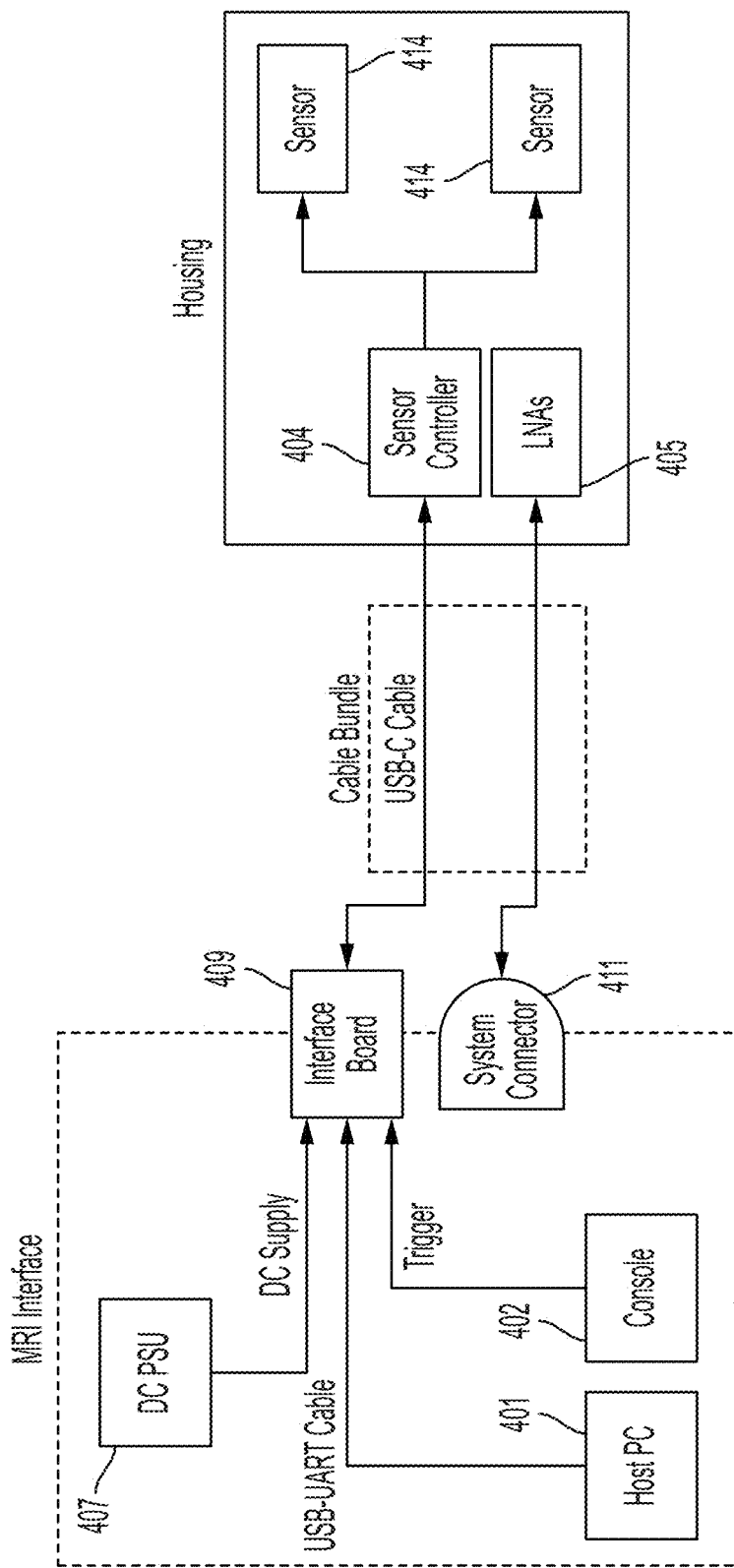
FIG. 4B illustrates exemplary devices for detecting motion of a patient in communication with an MRI system, in accordance with some embodiments of the technology described herein.

FIG. 4B illustrates exemplary devices for detecting motion of a patient in communication with an MRI system, in accordance with some embodiments of the technology described herein. In some embodiments, sensor controller 404 may be coupled to one or more sensors 414, as described in connection with FIG. 4A herein. The sensor controller 404 and sensors 414 may be disposed within a housing configured to accept a part of a patient's anatomy (e.g., head, limb, knee, foot, ankle, etc.). For example, the housing may be configured to fit within the MRI system and to accept a head of the patient, as described herein, including with reference to FIGS. 10A-10E, or to accept a foot of the patient, as described herein including with reference to FIG. 11.

In some embodiments, one or more low noise amplifiers (LNAs) 405 may also be disposed within the housing adjacent the sensor controller 404. The LNAs 405 may be configured to amplify MR signals detected by the RF coils (e.g., from RF transmit and receive coils 126 of FIG. 1) while introducing a small or minimal level of noise to the measurements. The LNAs may be communicatively coupled to the MRI interface through system connector 411.

In some embodiments, the sensor controller 404 may be communicatively coupled to the MRI system interface by a cable. For example, the sensor controller 404 may be digitally communicatively coupled to the MRI system interface through a universal serial bus (USB) cable (e.g., a USB-C cable, as shown in the example of FIG. 4B). It should be appreciated that the sensor controller 404 may, in some embodiments, be communicatively coupled to the MRI system using a different type of cable and/or using an analog connection. In some embodiments, the cables connecting the sensor controller 404 and the LNAs 405 to the MRI interface may be bundled to form a single cable bundle.

In some embodiments, the sensor controller 404 may be communicatively coupled to an interface board 409 configured to communicate with components of the MRI system interface. The interface board 409 may be a printed circuit board (PCB), in some embodiments, configured to communicate signals from various components of the MRI system interface to the sensor controller 404. In some embodiments, the interface board 409 may be communicatively coupled to a host PC 401, a console 402, and/or a DC power supply (PSU) 407. In some embodiments, the host PC 401 may be communicatively coupled to the interface board 409 with a USB to universal asynchronous receiver-transmitter (UART) cable for serial interfacing with the interface board 409.

In some embodiments, the console 402 may be the same console as described in connection with FIG. 4A herein. The console 402 may be communicatively coupled to the sensor controller 404 (e.g., through the interface board 409). In some embodiments, the console 402 may be configured to send one or more trigger signals to the sensor controller 404 through the interface board 409. For example, the console 402, in some embodiments, may send the Tx/Rx trigger signal 403 to sensor controller 404 through the interface board 409 to maintain synchronicity between the MRI system and the sensors 414.

In some embodiments, the DC PSU 407 may provide power to components of the sensor controller 404 and/or sensors 414. The DC PSU 407 may be configured to supply the interface board 409, sensor controller 404, and/or sensors 414 with DC power. For example, the DC power may be used to power components of the sensor controller 404, including PSoC 406, RF source 408, couplers 410, and/or detectors 412.

Figure 6A:
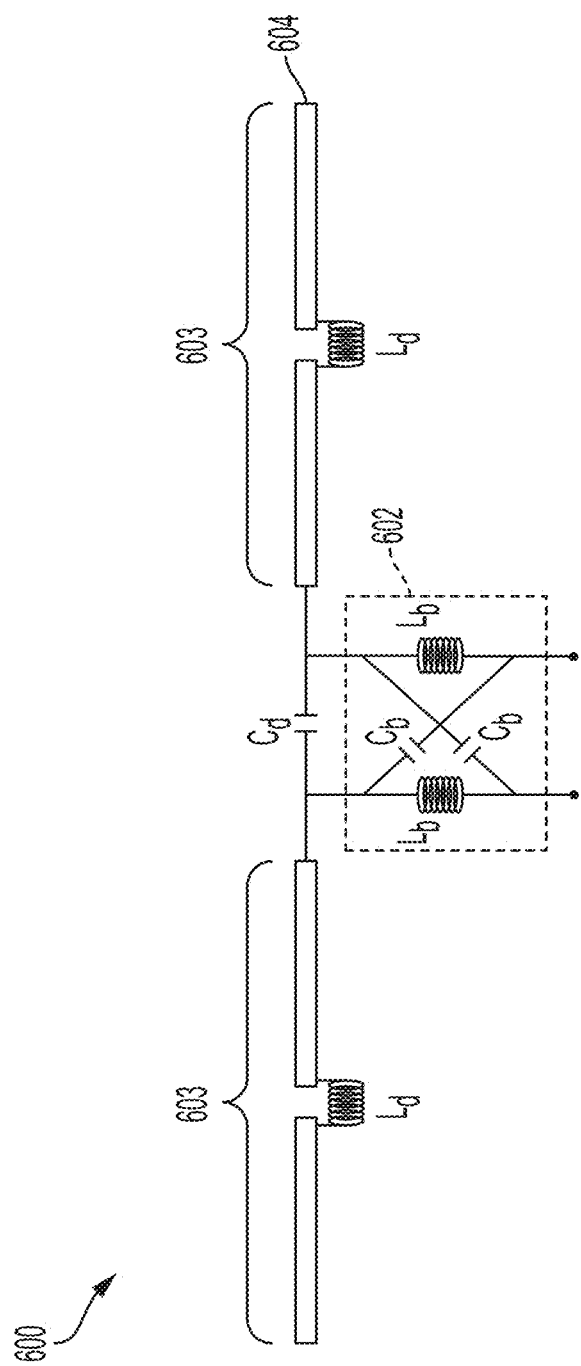
FIG. 6A illustrates exemplary components of an illustrative sensor for detecting motion of a patient, in accordance with some embodiments of the technology described herein.

FIG. 6A illustrates a sensor 600a, in accordance with some embodiments. Sensor 600a may be implemented as sensor 414 of device 400, as described in connection with FIGS. 4A and 4B. Sensor 600a may be formed as a dipole antenna including a lattice balun 602 and conductors 604, according to some embodiments. Terminals of lattice balun 602 may be connected to a coaxial cable, the coaxial cable providing a driving RF signal to sensor 600a. Lattice balun may include inductors $L_b$ and capacitors $C_b$ enabling the driving of a symmetric differential voltage across capacitor Cd. Changing the value of capacitor Cd may change an impedance of sensor 600a. In some embodiments, sensor 600a has an impedance of 50 Ohms.

Lattice balun 602 may be coupled to two arms 603, each arm 603 having lengths of conductors 604 separated by inductors $L_d$, in accordance with some embodiments. The length of sensor 600a may be determined by the desired frequency. A lowest resonant frequency of a dipole antenna such as sensor 600a may occur when the electrical length of the dipole is half as long as the desired wavelength. For example, the physical length of sensor 600a may be 91 cm to be sensitive to a signal with a frequency of 165 MHz.

Inductors $L_d$ placed in series with conductors 604 may reduce the physical length of sensor 600a while maintaining a desired electrical length. By including inductors $L_d$, sensor 600a may be made much more physically compact.

Figure 6B:
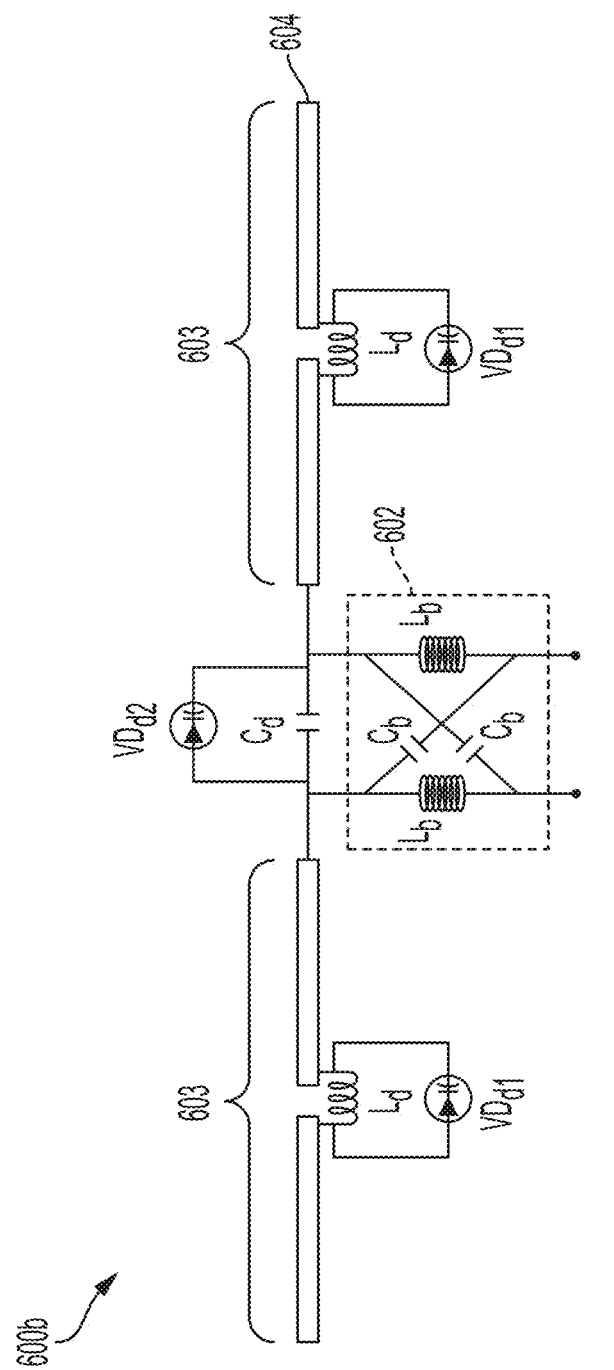
FIG. 6B illustrates exemplary components of another illustrative sensor for detecting motion of a patient, in accordance with some embodiments of the technology described herein.

FIG. 6B illustrates another example of a sensor 600b, in accordance with some embodiments of the technology described herein. Sensor 600b may be implemented as sensor 414 of device 400, as described in connection with FIGS. 4A and 4B. Sensor 600b may be the same as the sensor 600a but may include varactor diodes $VD_{d1}$ placed in parallel with inductors $L_d$ of sensor 600b. In some embodiments, the capacitance of the varactor diodes $VD_{d1}$ may be electronically tuned (e.g., by changing a voltage applied to the varactor diode) to change a center frequency of the sensor 600b.

In some embodiments, sensor 600b may optionally include a second varactor diode $VD_{d2}$. The second varactor diode $VD_{d2}$ may be placed in parallel with capacitor Cd. In such embodiments, the capacitance of the second varactor diode $VD_{d2}$ may be tuned electronically (e.g., by changing a voltage applied to the varactor diode) to perform impedance matching of the sensor 600b.

Figure 7:
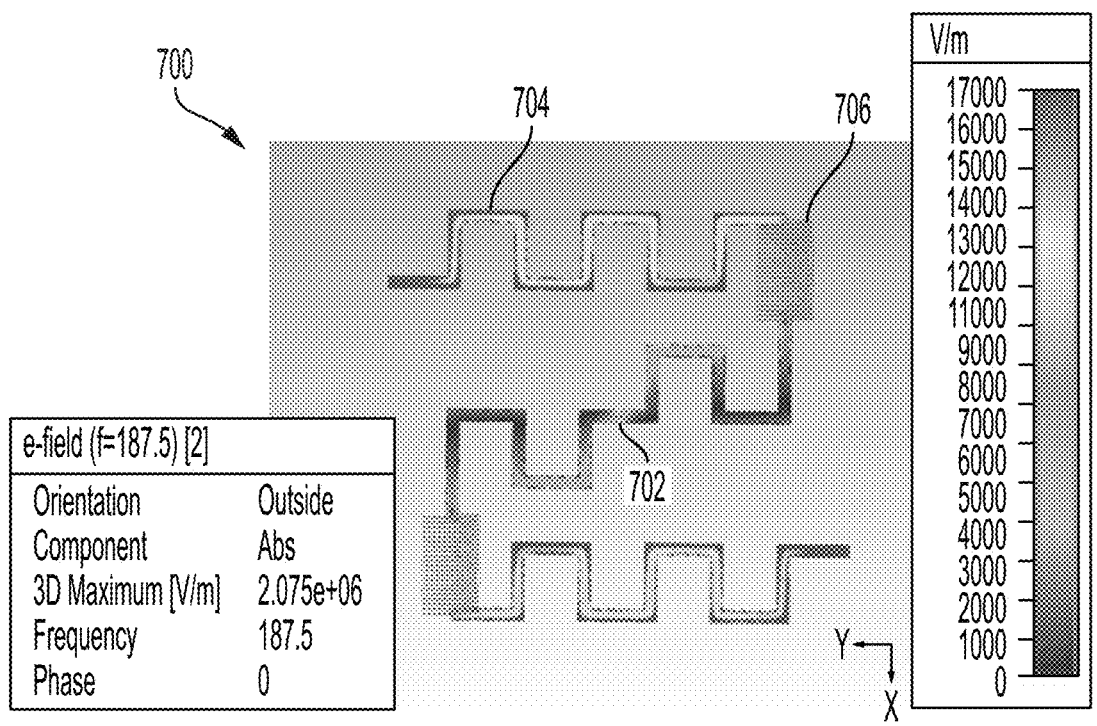
FIG. 7 illustrates a simulated voltage distribution of a sensor for detecting motion of a patient, in accordance with some embodiments of the technology described herein.

Alternatively or additionally, sensors 600a or 600b may be made in a compact form factor, as shown in FIG. 7. FIG. 7 illustrates a simulated voltage distribution of a sensor 700, in accordance with some embodiments. The gradient regions of sensor 700 indicate voltage distribution within sensor 700. Sensor 700 may be implemented as sensor 414 of device 400, as described in connection with FIG. 4A.

In some embodiments, sensor 700 may be a dipole antenna that is folded to fit within a 3 cm×3 cm area. A lattice balun 702 is represented in the simulation of FIG. 7 as an input port for a driving RF signal. Conductors 704 may be coupled to lattice balun 702 by inductors 706, which are simulated as areas of additional physical length.

Figure 8:
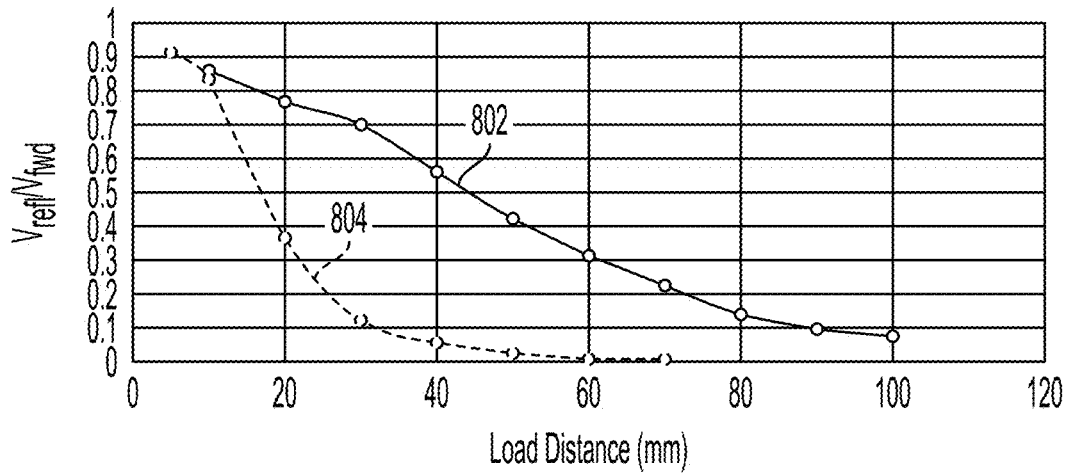
FIG. 8 illustrates a measured linear reflection coefficient as a function of distance between different sensors and a capacitive load, in accordance with some embodiments of the technology described herein.

In some embodiments, sensor 700 may detect a patient's presence when the patient is within approximately 4 cm of sensor 700. A range of a dipole sensor may be related to a physical size of the dipole sensor, as shown in FIG. 8. FIG. 8 illustrates the measured reflection coefficient, $V_{ref}/V_{fwd}$, as a function of distance between different sized sensors and a capacitive load, in accordance with some embodiments. Curve 802 was measured from a sensor with a configuration like that of sensor 600 while curve 804 was measured from a sensor with a configuration like that of sensor 700. As a sensor becomes more compact in arrangement, its physical range may be reduced.

Figure 9:
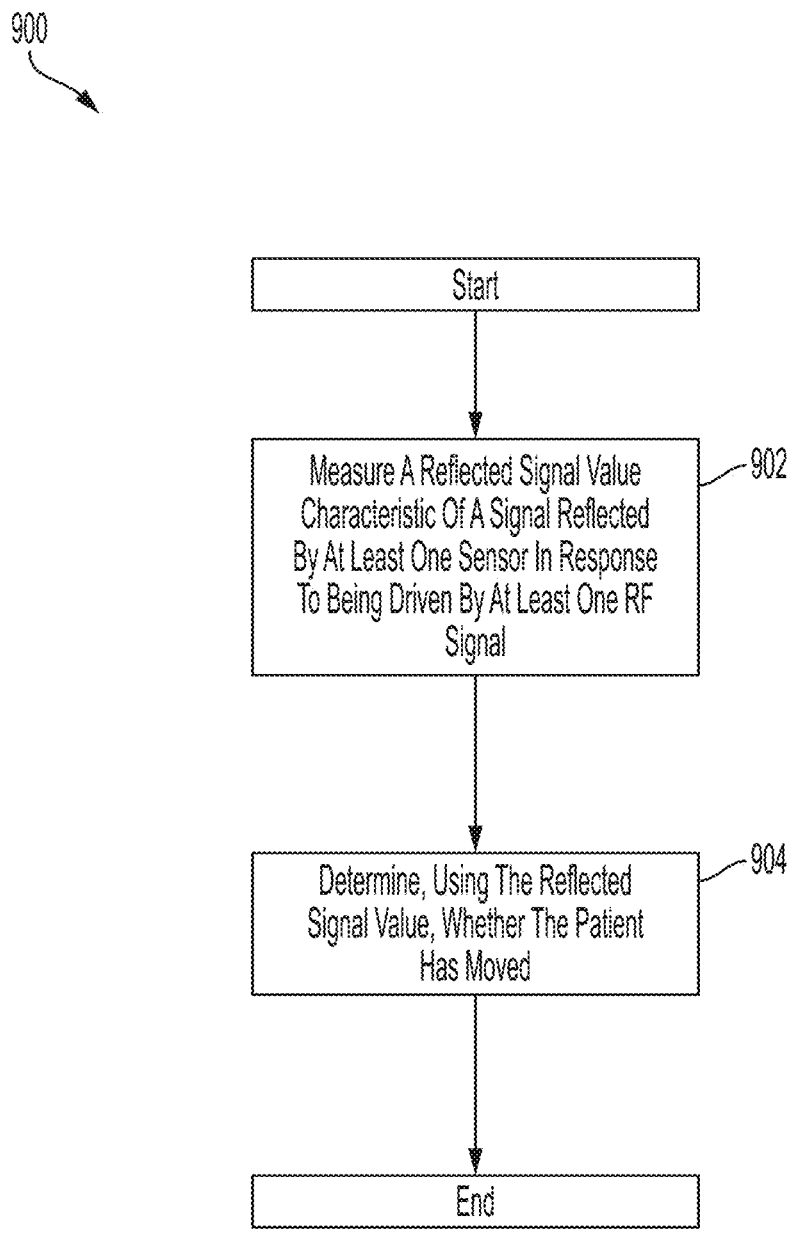
FIG. 9 is a flowchart of an illustrative process 900 for determining whether a patient has moved, in accordance with some embodiments of the technology described herein.

FIG. 9 is a flowchart of an illustrative process 900 for detecting whether a patient positioned within an MRI system has moved, in accordance with some embodiments of the technology described herein. For example, the process 900 may be performed by device 400 described with reference to FIG. 4A. In some embodiments, the process 900 may be performed by hardware (e.g., using an ASIC, an FPGA, or any other suitable circuitry), software (e.g., by executing the software using a computer processor), or any suitable combination thereof.

In act 902, a reflected signal value may be measured from at least one sensor capacitively coupled to a patient positioned within an MRI system. The at least one sensor may be, for example, one or more of sensors 414, 600, and/or 700 as described in connection with FIGS. 4, 6, and 7. The measured reflected signal value may be characteristic of a signal reflected by at least one sensor in response to being driven by at least one RF signal. For example, the reflected signal value may be a voltage of the signal reflected by the at least one sensor. The measured reflected signal value may also be indicative of a distance between the patient and the sensor, as described in connection with FIG. 5.

In some embodiments, a reflected signal value may be measured from the at least one sensor synchronously with processes performed by an MRI system. For example, a reflected signal value may be measured for each Tx/Rx pulse of an MR imaging procedure, as described in connection with FIG. 4A.

Next, in act 904, it may be determined, using the reflected signal value, whether the patient has moved while positioned within the MRI system. In some embodiments, determining whether the patient has moved may be performed by at least one processor (e.g., a processor of console 402 as described in connection with FIG. 4A).

In some embodiments, determining whether the patient has moved may include calculating a ratio of the reflected signal value from the at least one sensor to a signal value of the RF signal driving the sensor. The calculated ratio may be compared to a threshold value to determine whether the patient has moved while positioned within the MRI system. The threshold value may be based on, for example, a measured ratio for the sensor when a patient is not positioned within the MRI system.

Figure 10A:
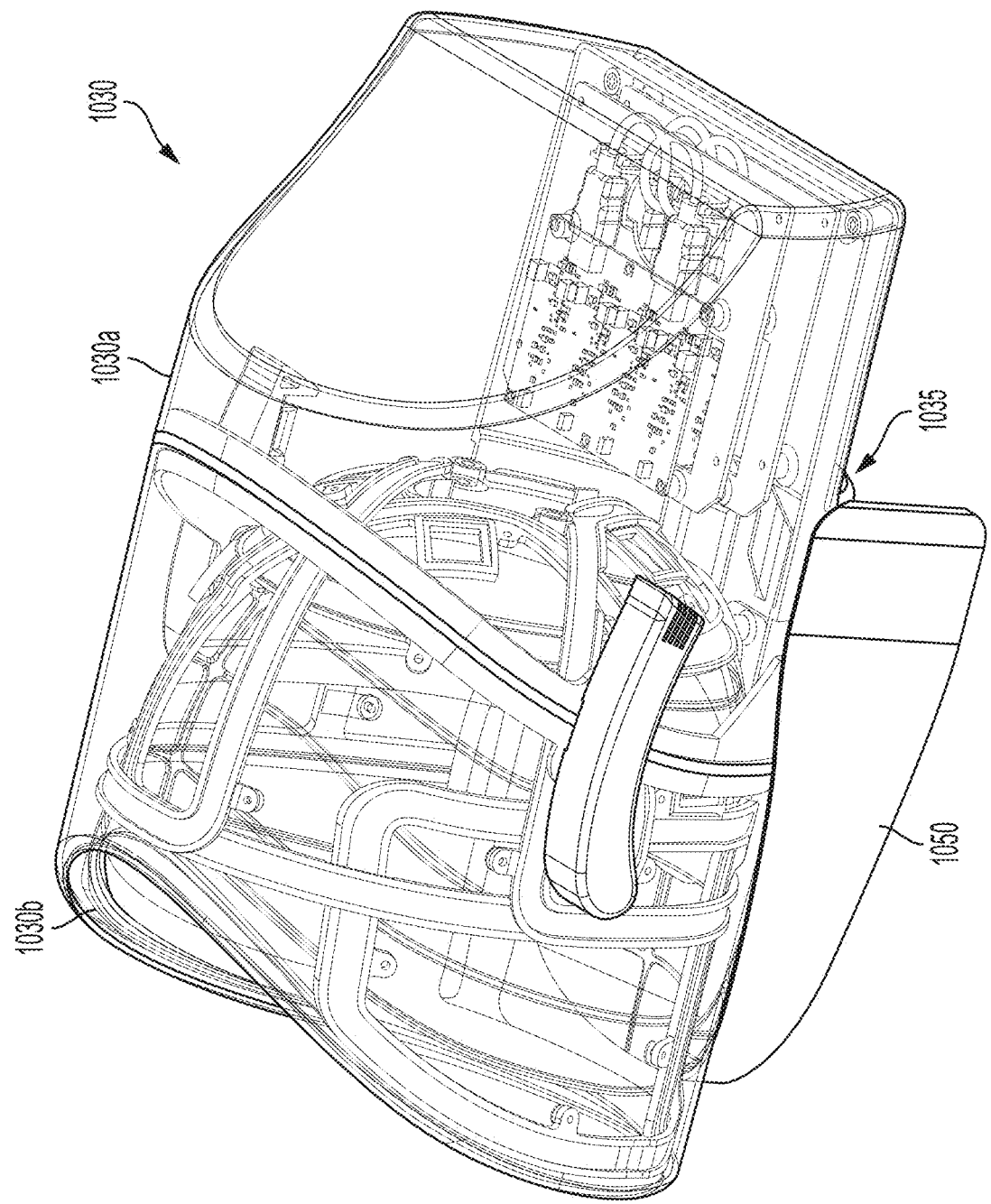
FIGS. 10A and 10B illustrate a helmet configured to accommodate a patient's head during MR imaging, in accordance with some embodiments of the technology described herein.
Figure 10B:
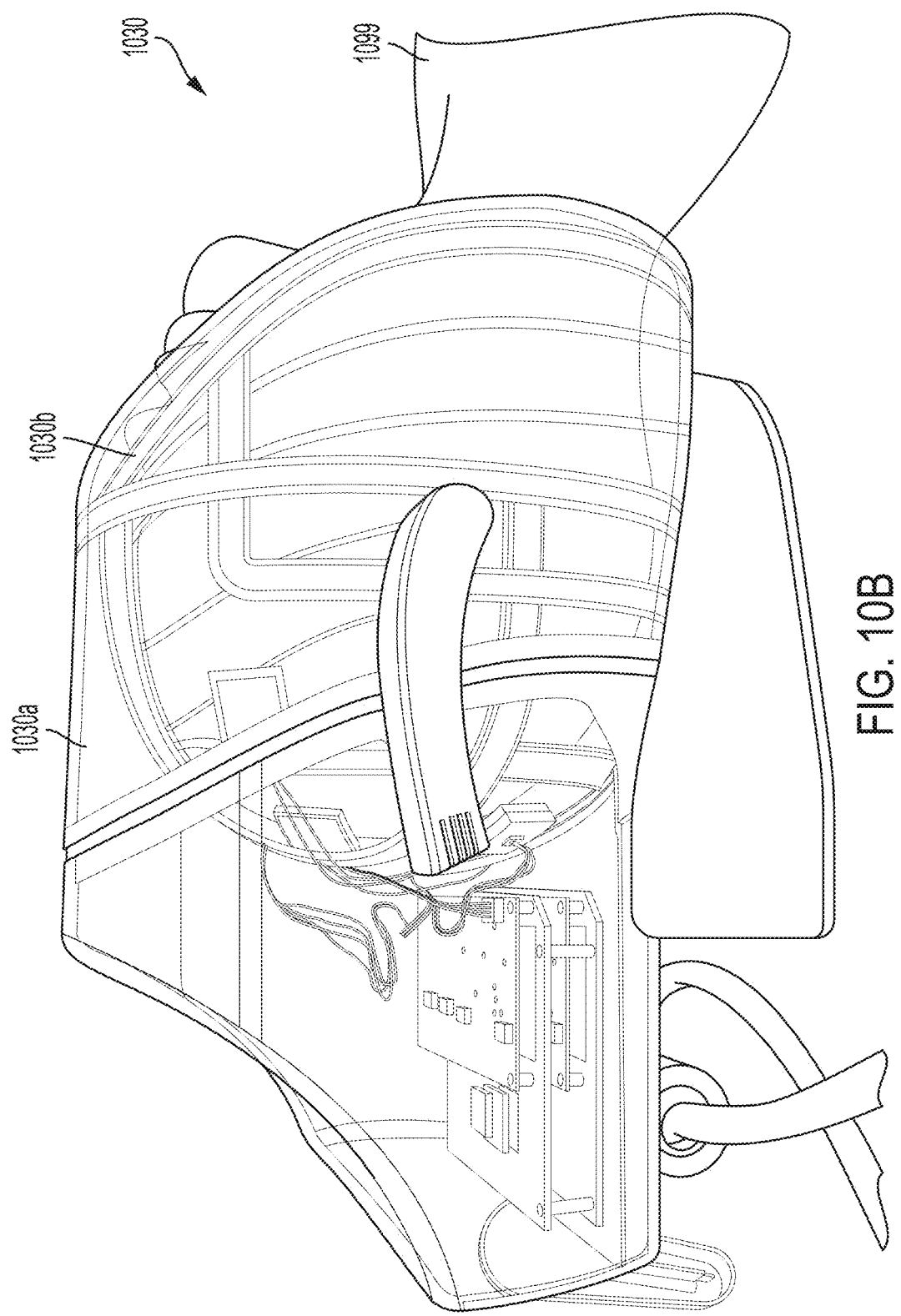

In some embodiments, sensors may be included in components configured to receive a portion of a patient's anatomy. FIGS. 10A and 10B illustrate a helmet 1030 to assist medical personnel in properly positioning a patient within helmet 1030, which is further described in U.S. patent application Ser. No. 16/516,373 filed Jul. 19, 2019, and titled "Methods and Apparatus for Patient Positioning in Magnetic Resonance Imaging," which is incorporated by reference in its entirety herein. According to some embodiments, helmet 1030 comprises an outer housing 1030*a* and a coil support 1030*b* for transmit and/or receive coils. Coil support 1030*b* may be adapted to accommodate a patient's head and provide a surface to which the transmit and/or receive coils are disposed. Housing 1030*a* may be attached to base 1050 comprising a releasable securing mechanism 1035 to releasably secure helmet 1030 to an MRI system within the imaging region of the system.

FIG. 10B illustrates a radio frequency helmet 1030 with a patient 1099 positioned within coil support 1030*b*. Because outer housing 1030*a* and coil support 1030*b* are see-through (e.g., constructed from a transparent or semi-transparent plastic material), the patient's head can be viewed through helmet 1030, thus facilitating proper positioning of patient 1099 within helmet 1030.

Figure 10C:
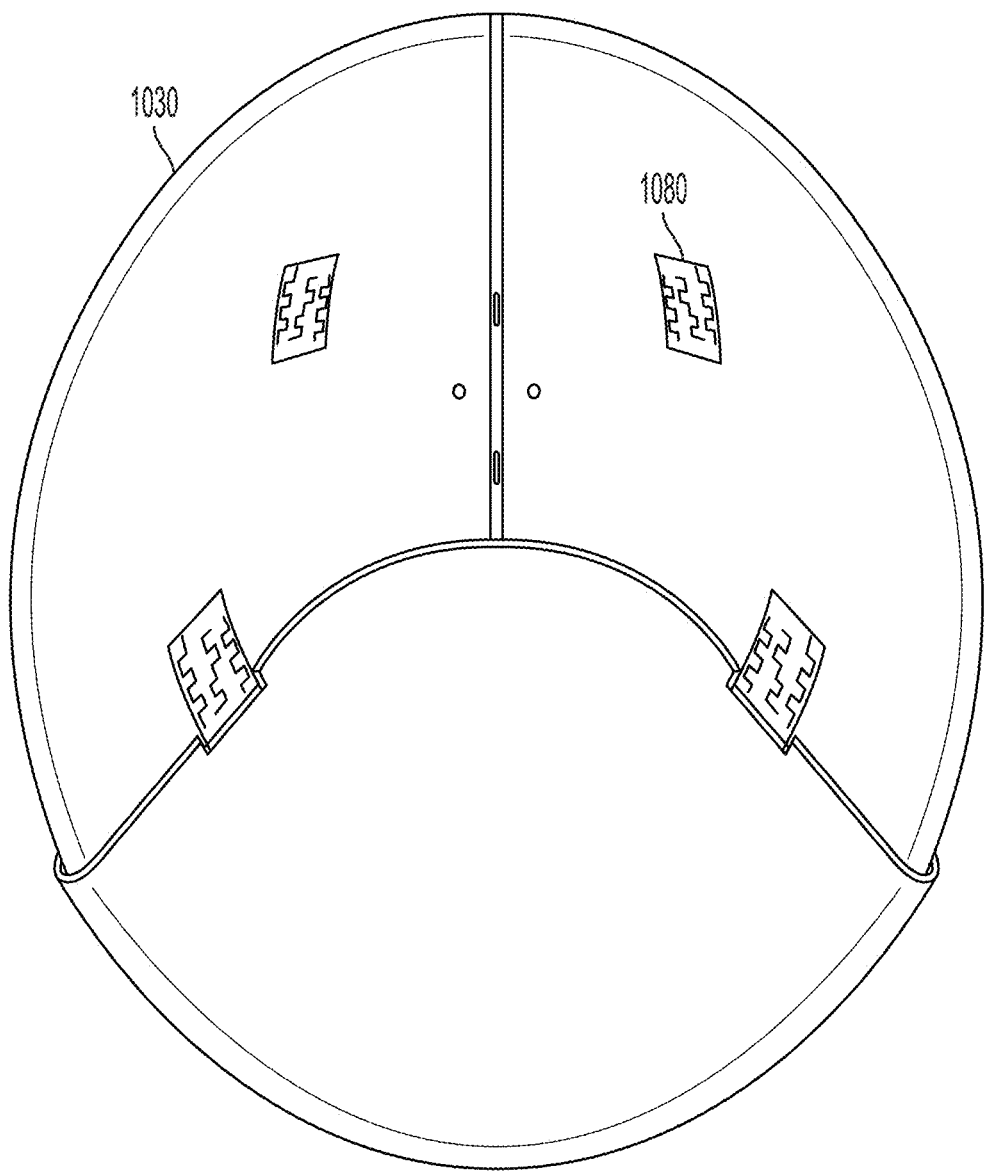
FIG. 10C illustrates a helmet configured to accommodate a patient's head during MR imaging and including sensors for detecting motion by the patient during imaging, in accordance with some embodiments of the technology described herein.

FIG. 10C shows an interior view of a helmet 1030 with sensors 1080 disposed on a surface of the helmet 1030, in accordance with some embodiments. FIG. 10D shows a perspective view of helmet 1030 showing sensors 1080 positioned on a surface of the helmet and arranged around a patient's head. Sensors 1080 may be RF sensors such as those described in connection with FIGS. 6 and 7 herein (e.g., antennas or dipole antennas). In particular, in the embodiment illustrated in FIG. 10C, the sensors 1080 may be disposed on opposing surfaces of helmet 1030 so that the patient's head may be placed centrally between sensors 1080. In some embodiments, the sensors may be integrated within the helmet 1030.

It may be appreciated that the arrangement of sensors shown in FIG. 10C is only one example and that other arrangements of sensors may be implemented depending on the type and/or direction of motion that is desirable to detect. For instance, the arrangement of sensors 1080 as shown in FIGS. 10C and 10D may be used to detect motion of the patient's head when it makes side-to-side motions (e.g., shaking the head "no") and/or nodding motions (e.g., nodding the head "yes"). It may also be desirable to monitor up-down motion of the patient's head (e.g., into and out of the helmet), and sensors 1080 may be placed at the top of the interior surface of helmet 1030 to monitor such motion. In some embodiments, where it is desired to detect motion in six degrees of freedom (e.g., translation in three directions and rotations about three axes), there may be at least six sensors 1080 included in the arrangement.

Figure 10E:
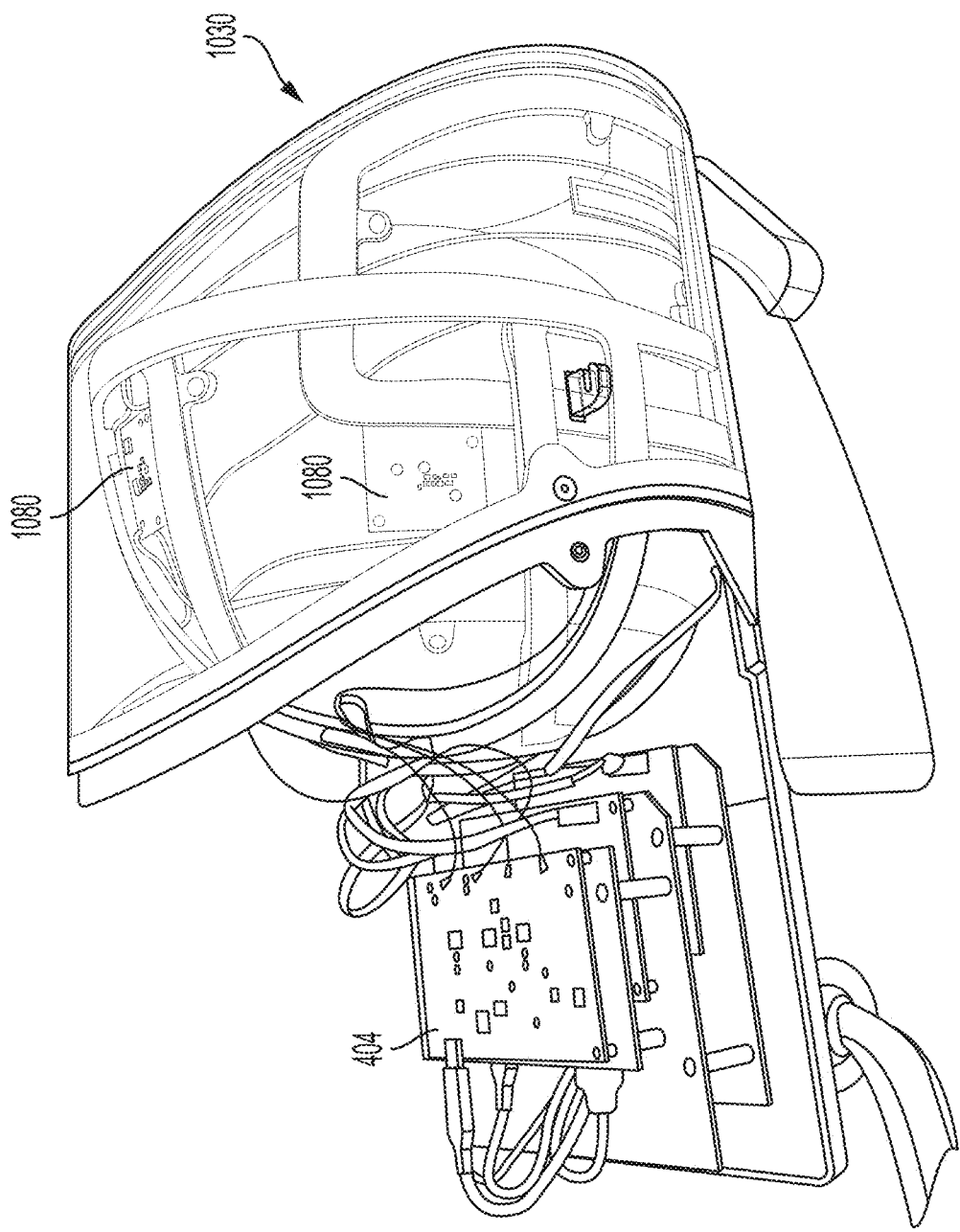
FIG. 10E illustrates another example of a helmet configured to accommodate a patient's head during MR imaging and including sensors for detecting motion by the patient during imaging and a sensor controller, in accordance with some embodiments of the technology described herein.

Additionally or alternatively, the sensor controller 404 may be located adjacent the sensors, in some embodiments, as shown in the example of FIG. 10E. FIG. 10E illustrates another example of a helmet 1030 configured to accommodate a patient's head during MR imaging. The helmet 1030 may include both sensors 1080 for detecting motion by the patient during imaging and a sensor controller 404, in accordance with some embodiments of the technology described herein. By placing the sensor controller 404 near the sensors 1080, cabling configured to transmit the analog signals from the sensors 1080 to the sensor controller 404 may be shorter in length, reducing RF interference with the signals and improving performance of the motion detection system.

FIG. 10F illustrates another view of a helmet disposed within an MRI system, in accordance with some embodiments of the technology described herein. In some embodiments, the components of helmet 1030 (e.g., sensor controller 404 and/or sensors 1080, not pictured) may be communicatively coupled from within the MRI system (e.g., within the imaging region of the MRI system) to an external MRI interface by a cable bundle 1090. The cable bundle may include portions 1090*a*, 1090*b* to provide communicative coupling from the MRI interface to different components of helmet 1030 (e.g., as described in connection with FIG. 4B herein). For example, portion 1090*a* may include a USB cable to provide communicative coupling to the sensor controller 404, and portion 1090*b* may include an analog connection to provide communicative coupling to LNAs 405. In some embodiments, the portions 1090*a*, 1090*b* may be routed through a connector 1092 that is configured to also provide electrical coupling between the RF coils disposed within the helmet 1030 and the MRI interface.

Figure 11:
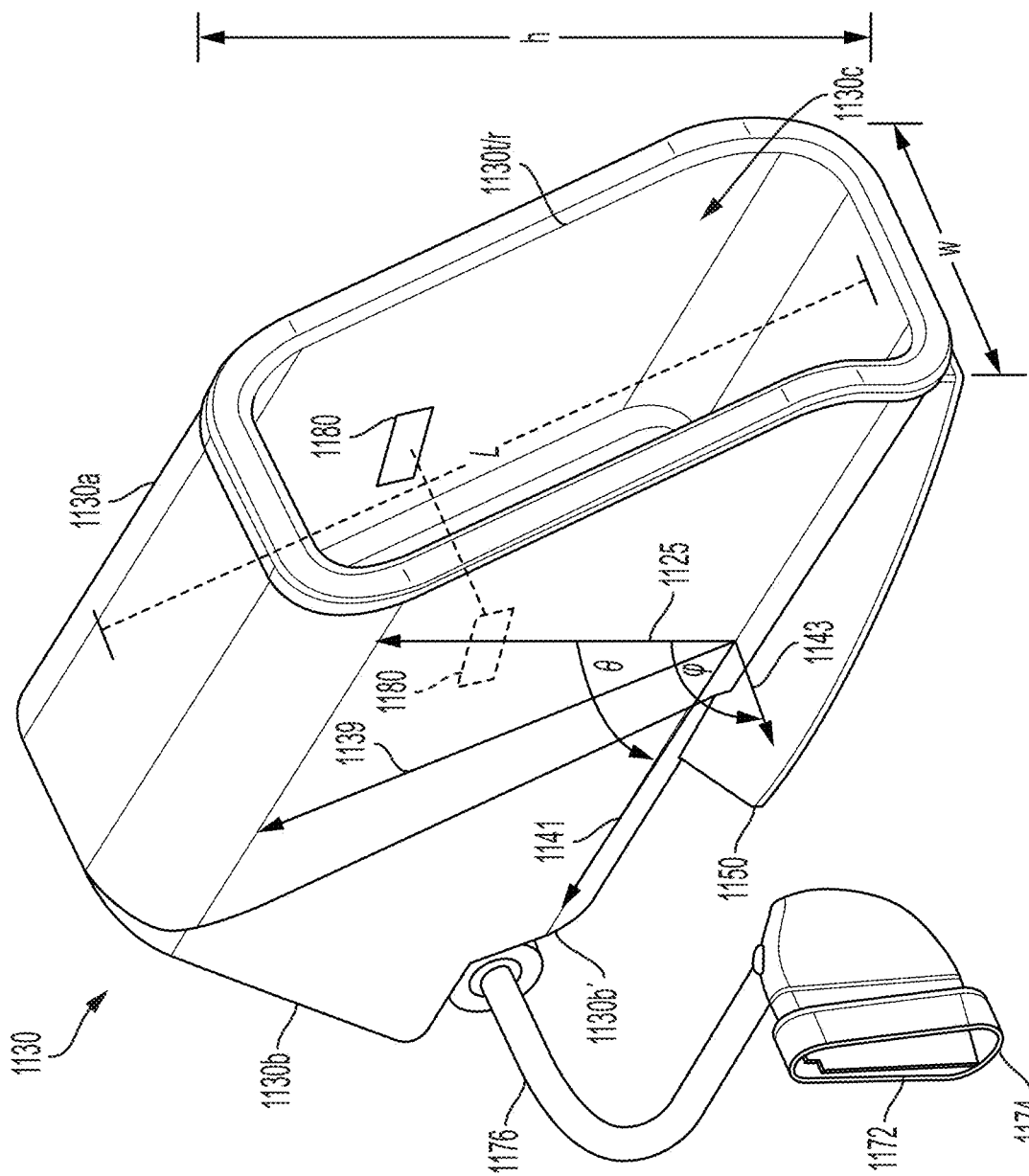
FIG. 11 illustrates a device configured to accommodate a patient's foot during MR imaging and including sensors, in accordance with some embodiments of the technology described herein.

As described above, techniques for detecting motion of a patient within an MRI system may also be applied to a device configured to accommodate an appendage, such as a leg or an arm, or a portion of an appendage such as an ankle, foot, wrist, hand, etc. FIG. 11 illustrates aspects of a foot coil adapted to accommodate a foot, configured to secure the foot coil to an MRI system so that the foot is positioned within the imaging region of the MRI system (e.g., within the imaging region of the exemplary low-field MRI systems described in the foregoing), and is coupled with sensors configured to capacitively couple with the patient's foot. According to some embodiments, a radio frequency apparatus is adapted to accommodate a foot and configured to be secured within the imaging region of an MRI system having a bi-planar $B_0$ magnet configuration in which the space between upper and lower $B_0$ magnets may be limited, some examples of which are described in further detail below.

FIG. 11 illustrates a view of a radio frequency apparatus 1130 (referred to generally herein as a "foot coil," adapted to accommodate a foot for one or more MRI procedures). Foot coil 1130 comprises transmit/receive housings or supports 1130*t/r* on or within which transmit and/or receive coils for the radio frequency apparatus are provided. According to some embodiments, foot coil 1130 comprises a transmit housing for transmit coils and a receive housing for receive coils, as described in further detail in U.S. Patent Application No. 62/811,361, titled "Methods and Apparatus for Patient Position in Magnetic Resonance Imaging" filed Feb. 27, 2019, which is incorporated by reference in its entirety herein.

Exemplary foot coil 1130 also comprises an outer housing 1130a to at least partially cover transmit/receive housing(s) 1130t/r and to form a volume 1130c adapted to accommodate a foot. As illustrated in FIG. 11A, volume 1130c has a height h and a w that allows a foot to be inserted into the interior of foot coil 1130. FIG. 11 illustrates sensors 1180 coupled to foot coil 1130 of FIG. 11A, in accordance with some embodiments described herein. Sensors 1180 may be RF sensors such as those described in connection with FIGS. 6 and 7 herein (e.g., dipole antennas). In particular, in the embodiment illustrated in FIG. 11, the sensors 1180 may be disposed on opposing surfaces of foot coil 1130 so that the patient's foot may be placed between sensors 1180.

It may be appreciated that the arrangement of sensors shown in FIG. 11 is only one example and that other arrangements of sensors may be possible depending on the type and/or direction of motion is desirable to detect. For instance, the arrangement of sensors 1180 may be used to detect motion of the patient's foot along a latitudinal axis 1143, but additionally it may be desirable to detect motion of the patient's foot relative to a podal axis 1139. To detect motion of the patient's foot relative to the podal axis 1139, additional sensors may be arranged relative to the podal axis 1139 (e.g., along an axis perpendicular to the podal axis 1139 or along an axis at any other angle relative to the podal axis 1139).

Figure 12:
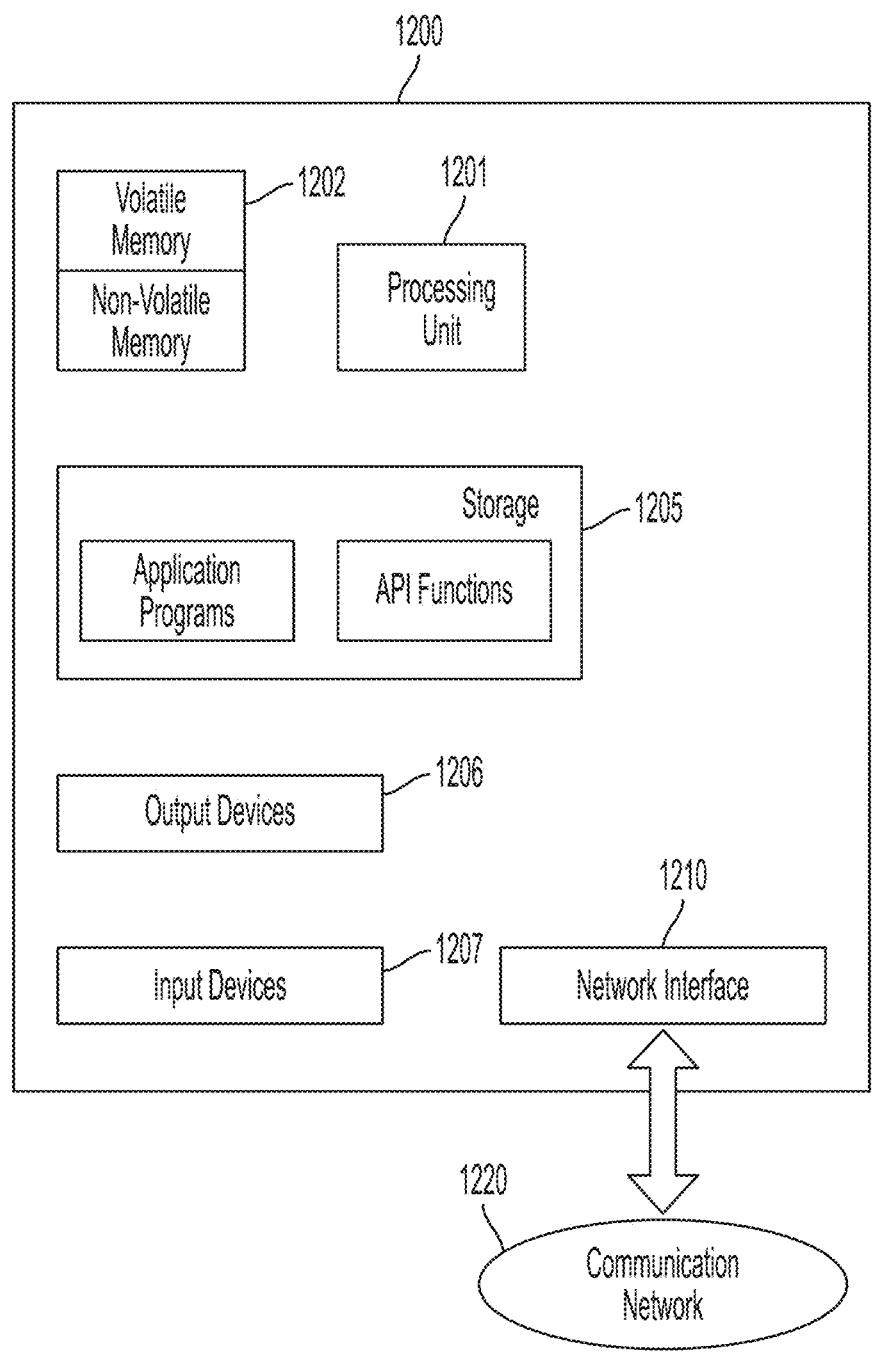
FIG. 12 depicts, schematically, an illustrative computing device on which aspects of the technology described herein may be implemented.

FIG. 12 shows, schematically, an illustrative computer 1200 on which any aspect of the present disclosure may be implemented.

In the embodiment shown in FIG. 12, the computer 1200 includes a processing unit 1301 having one or more processors and a non-transitory computer-readable storage medium 1302 that may include, for example, volatile and/or non-volatile memory. The memory 1302 may store one or more instructions to program the processing unit 1201 to perform any of the functions described herein. The computer 1200 may also include other types of non-transitory computer-readable medium, such as storage 1205 (e.g., one or more disk drives) in addition to the system memory 1202. The storage 1205 may also store one or more application programs and/or resources used by application programs (e.g., software libraries), which may be loaded into the memory 1202.

The computer 1200 may have one or more input devices and/or output devices, such as devices 1206 and 1207 illustrated in FIG. 12. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards and pointing devices, such as mice, touch pads, and digitizing tablets. As another example, the input devices 1207 may include a microphone for capturing audio signals, and the output devices 1206 may include a display screen for visually rendering, and/or a speaker for audibly rendering, recognized text. As another example, the input devices 1207 may include sensors (e.g., electrodes in a pacemaker), and the output devices 1206 may include a device configured to interpret and/or render signals collected by the sensors (e.g., a device configured to generate an electrocardiogram based on signals collected by the electrodes in the pacemaker).

As shown in FIG. 12, the computer 1200 may also comprise one or more network interfaces (e.g., the network interface 1210) to enable communication via various networks (e.g., the network 1220). Examples of networks include a local area network or a wide area network, such as an enterprise network or the Internet. Such networks may be based on any suitable technology and may operate according to any suitable protocol and may include wireless networks, wired networks or fiber optic networks. Such networks may include analog and/or digital networks.

Having thus described several aspects of at least one embodiment of this technology, it is to be appreciated that various alterations, modifications, and improvements will readily occur to those skilled in the art.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semi-custom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Also, the various methods or processes outlined herein may be coded as software that is executable on one or more processors running any one of a variety of operating systems or platforms. Such software may be written using any of a number of suitable programming languages and/or programming tools, including scripting languages and/or scripting tools. In some instances, such software may be compiled as executable machine language code or intermediate code that is executed on a framework or virtual machine. Additionally, or alternatively, such software may be interpreted.

The techniques disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more processors, perform methods that implement the various embodiments of the present disclosure described above. The computer-readable medium or media may be transportable, such that the program or programs stored thereon may be loaded onto one or more different computers or other processors to implement various aspects of the present disclosure as described above.

The terms "program" or "software" are used herein to refer to any type of computer code or set of computer-executable instructions that may be employed to program one or more processors to implement various aspects of the present disclosure as described above. Moreover, it should be appreciated that according to one aspect of this embodiment, one or more computer programs that, when executed, perform methods of the present disclosure need not reside on a single computer or processor, but may be distributed in a modular fashion amongst a number of different computers or processors to implement various aspects of the present disclosure.

Various aspects of the technology described herein may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as a method, examples of which are provided herein including with reference to FIG. 9. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The terms "approximately" and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

What is claimed is:

1. A device configured to accommodate a patient's anatomy during magnetic resonance (MR) imaging, the device comprising:
   at least one radio frequency (RF) transmit and/or receive coil;
   at least one sensor, different from the at least one RF transmit and/or receive coil, configured to be capacitively coupled to the patient during MR imaging separately from the at least one RF transmit and/or receive coil; and
   a housing supporting the at least one RF transmit and/or receive coil and the at least one sensor,
   wherein the device is configured to drive the at least one sensor with at least one RF signal and measure a reflected signal value from the at least one sensor.

2. The device of claim 1, wherein the at least one sensor comprises at least one RF sensor.

3. The device of claim 2, wherein the at least one RF sensor is configured to resonate at a frequency between 100 MHz and 250 MHz.

4. The device of claim 2, wherein the at least one RF sensor comprises at least one RF antenna.

5. The device of claim 4, wherein the at least one RF antenna comprises at least one RF dipole antenna.

6. The device of claim 5, wherein:
   the at least one dipole antenna comprises four dipole antennas; and
   the housing is an outer housing of a helmet configured to accommodate the patient's head during MR imaging, and wherein the four dipole antennas are coupled to the helmet.

7. The device of claim 6, wherein the four dipole antennas are positioned on an inner surface of the helmet and arranged in two sets of two dipole antennas each, wherein:
   the dipole antennas of each set of two dipole antennas are disposed along a respective axis; and
   the patient's head is located on the respective axis between the dipole antennas of each set of two dipole antennas.

8. The device of claim 5, wherein:
   the at least one dipole antenna comprises at least one inductor coupled to a lattice balun; and
   the at least one inductor is coupled to the lattice balun through at least a portion of a conductive arm of the at least one dipole antenna, and wherein the at least one inductor is configured to reduce the physical length of the at least one dipole antenna.

9. The device of claim 8, wherein the at least one dipole antenna comprises at least one varactor diode coupled in parallel with the at least one inductor.

10. The device of claim 5, wherein:
    the at least one dipole antenna comprises at least one inductor coupled to a lattice balun; and
    the at least one dipole antenna comprises at least one conductive arm, the at least one conductive arm including at least one 90-degree bend.

11. The device of claim 1, wherein the housing is an outer housing configured to accommodate a patient's foot during MR imaging.

12. The device of claim 1, wherein the housing is an outer housing configured to accommodate a patient's head during MR imaging.

13. A device configured to accommodate a patient's anatomy during magnetic resonance (MR) imaging, the device comprising:
    at least one radio frequency (RF) transmit and/or receive coil;
    at least one sensor, different from the at least one RF transmit and/or receive coil, configured to be capacitively coupled to the patient during MR imaging separately from the at least one RF transmit and/or receive coil; and
    a helmet comprising a housing supporting the at least one RF transmit and/or receive coil and the at least one sensor.

14. The device of claim 1, further comprising an attachment mechanism configured to couple the device with an MR imaging system.

15. A device configured to accommodate a patient's anatomy during magnetic resonance (MR) imaging by a magnetic resonance imaging (MRI) system, the MM system comprising at least one RF transmit and/or receive coil, the device comprising:
    at least one RF sensor, different from the at least one RF transmit and/or receive coil of the MRI system, configured to be capacitively coupled to the patient, separately from the at least one RF transmit and/or receive coil of the MRI system, that is positioned in the imaging region for determining whether the patient moved during MR imaging;

an attachment mechanism configured to couple the device with the MM system; and a helmet having a surface, wherein the at least one RF sensor is disposed on the surface.

16. The device of claim 15, wherein the at least one RF sensor is configured to resonate at a frequency between 100 MHz and 250 MHz.

17. The device of claim 15, wherein the at least one RF sensor comprises at least one RF antenna.

18. The device of claim 17, wherein the at least one RF antenna comprises at least one RF dipole antenna.

19. The device of claim 18, wherein the at least one dipole antenna comprises at least one inductor coupled to a lattice balun.

20. The device of claim 19, wherein the at least one inductor is coupled to the lattice balun through at least a portion of a conductive arm of the at least one dipole antenna, and wherein the at least one inductor is configured to reduce the electrical length of the at least one dipole antenna.

21. The device of claim 20, wherein the at least one dipole antenna comprises at least one varactor diode coupled in parallel with the at least one inductor.

22. The device of claim 19, wherein the at least one dipole antenna comprises at least one conductive arm, the at least one conductive arm including at least one 90-degree bend.

23. The device of claim 15, wherein the device is configured to accommodate a patient's foot during MR imaging.

24. The device of claim 15, wherein the device is configured to accommodate a patient's head during MR imaging.

25. The device of claim 15, wherein the at least one RF sensor comprises four RF sensors, the four RF sensors being arranged in two sets of two RF sensors each, wherein:
the RF sensors of each set of two RF sensors are disposed along an axis; and
the patient's head is located on the axis between the RF sensors of each set of two RF sensors.

26. A magnetic resonance imaging (MRI) system configured to capture a magnetic resonance (MR) image, the MRI system comprising:
a $B_0$ magnet configured to provide at least a portion of a $B_0$ field; and
the device of claim 1.

27. The device of claim 1, wherein the at least one sensor comprises a first RF sensor configured to resonate at a different frequency than the RF transmit and/or receive coil.

28. A device configured to accommodate a patient's anatomy during magnetic resonance (MR) imaging, the device comprising:
at least one radio frequency (RF) transmit and/or receive coil;
at least one sensor, different from the at least one RF transmit and/or receive coil, positioned within capacitive coupling range of the patient during MR imaging; and
a housing supporting the at least one RF transmit and/or receive coil and the at least one sensor,
wherein the device is configured to drive the at least one sensor with at least one RF signal and measure a reflected signal value from the at least one sensor.

29. The device of claim 28, wherein the at least one sensor comprises at least one RF sensor configured to be capacitively coupled to the patient during MR imaging when the patient is within capacitive coupling range of the at least one RF sensor.

* * * * *